US008868173B2

(12) United States Patent
Nelson et al.

(10) Patent No.: US 8,868,173 B2
(45) Date of Patent: Oct. 21, 2014

(54) METHOD AND APPARATUS FOR ASSESSING NEURAL ACTIVATION

(75) Inventors: Dwight E. Nelson, Shoreview, MN (US); Rahul Agarwal, Baltimore, MD (US); Steven L. Jensen, Andover, MN (US); Rahul Gupta, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 327 days.

(21) Appl. No.: 13/446,459

(22) Filed: Apr. 13, 2012

(65) Prior Publication Data
US 2012/0271189 A1    Oct. 25, 2012

Related U.S. Application Data

(60) Provisional application No. 61/477,356, filed on Apr. 20, 2011.

(51) Int. Cl.
*A61B 5/04* (2006.01)
*A61B 5/0476* (2006.01)
*A61N 1/36* (2006.01)
*A61N 1/372* (2006.01)
*A61B 5/0496* (2006.01)
*A61M 5/142* (2006.01)
*A61N 1/05* (2006.01)

(52) U.S. Cl.
CPC ......... *A61N 1/36139* (2013.01); *A61N 1/36067* (2013.01); *A61N 1/37247* (2013.01); *A61N 1/36185* (2013.01); *A61B 5/0496* (2013.01); *A61N 1/36132* (2013.01); *A61N 1/36175* (2013.01); *A61N 1/36171* (2013.01); *A61N 1/36153* (2013.01); *A61M 2005/14208* (2013.01); *A61B 5/0476* (2013.01); *A61M 5/14276* (2013.01); *A61N 1/0534* (2013.01)
USPC ............................................. 600/544; 607/2

(58) Field of Classification Search
CPC ............. A61B 5/0476; A61B 5/04012; A61B 5/04001; A61B 5/04; A61B 5/0482; A61N 1/372
USPC ................................................. 600/544, 545
See application file for complete search history.

(56) References Cited

U.S. PATENT DOCUMENTS 4,227,516 A    10/1980    Meland et al.
4,753,246 A    6/1988    Freeman
(Continued)

FOREIGN PATENT DOCUMENTS

WO    2004041069 A2    5/2004
WO    2004100765 A2    11/2004
WO    2011068947 A1    9/2011

OTHER PUBLICATIONS

Santaniello et al., "Closed-Loop Control of Deep Brain Stimulation: A Simulation Study", IEEE Transactions on Neural Systems and Rehabilitation Engineering, vol. 19, No. 1, Feb. 1, 2011, pp. 15-24.

(Continued)

*Primary Examiner* — Etsub Berhanu
(74) *Attorney, Agent, or Firm* — Medtronic, Inc.

(57) ABSTRACT

Various embodiments concern sensing a LFP signal from one or more electrodes, measuring the amplitude of the signals over a period of time, and calculating a plurality of variance values from the amplitude, wherein each of the variance values correspond to the variance of the amplitude for a different interval of time of the period of time with respect to the other variance values. Such embodiments may further include assessing the relative level of neural activation of an area of the brain based on the variance values, wherein the area of the brain is assessed to have a relatively higher level of neural activation when the variance is relatively higher and the area of the brain is assessed to have a relatively lower level of neural activation when the variance is relatively lower.

19 Claims, 6 Drawing Sheets

(56) References Cited

U.S. PATENT DOCUMENTS

| | | | |
|---|---|---|---|
| 4,776,345 A | 10/1988 | Cohen et al. | |
| 5,299,569 A | 4/1994 | Wernicke et al. | |
| 6,157,857 A | 12/2000 | Dimpfel | |
| 6,167,298 A | 12/2000 | Levin | |
| 6,200,273 B1 | 3/2001 | Sininger | |
| 6,227,203 B1 | 5/2001 | Rise et al. | |
| 6,402,520 B1 | 6/2002 | Freer | |
| 6,453,193 B1 | 9/2002 | Heyrend et al. | |
| 6,463,328 B1 | 10/2002 | John | |
| 6,615,076 B2 | 9/2003 | Mitra | |
| 6,920,351 B2 | 7/2005 | Mitra et al. | |
| 7,006,872 B2 | 2/2006 | Gielen et al. | |
| 7,089,059 B1 | 8/2006 | Pless | |
| 7,120,486 B2 | 10/2006 | Leuthardt | |
| 7,171,339 B2 | 1/2007 | Repucci | |
| 7,257,439 B2 | 8/2007 | Llinas | |
| 7,280,867 B2 | 10/2007 | Osorio et al. | |
| 7,341,562 B2 | 3/2008 | Pless | |
| 7,392,079 B2 | 6/2008 | Donoghue | |
| 7,409,321 B2 | 8/2008 | Repucci | |
| 7,532,935 B2 | 5/2009 | Maschino et al. | |
| 7,577,472 B2 | 8/2009 | Li et al. | |
| 7,626,015 B2 | 12/2009 | Feinstein | |
| 7,668,591 B2 | 2/2010 | Lee et al. | |
| 7,734,340 B2 | 6/2010 | DeRidder | |
| 7,747,318 B2 | 6/2010 | John | |
| 7,801,601 B2 | 9/2010 | Maschino et al. | |
| 7,818,065 B2 | 10/2010 | Llinas | |
| 7,819,812 B2 | 10/2010 | John | |
| 7,892,182 B2 | 2/2011 | Pless | |
| 7,894,890 B2 | 2/2011 | Sun et al. | |
| 7,894,903 B2 | 2/2011 | John | |
| 7,937,138 B2 | 5/2011 | Liley | |
| 8,017,764 B2 | 9/2011 | Feinstein | |
| 8,073,534 B2 | 12/2011 | Low | |
| 8,078,281 B2 | 12/2011 | Foffani | |
| 8,090,674 B2 | 1/2012 | Ginosar | |
| 8,140,152 B2 | 3/2012 | John | |
| 2001/0003145 A1 | 6/2001 | Mori et al. | |
| 2003/0191408 A1 | 10/2003 | Montgomery, Jr. | |
| 2004/0073129 A1 | 4/2004 | Caldwell et al. | |
| 2004/0073273 A1 | 4/2004 | Gluckman et al. | |
| 2004/0092809 A1 | 5/2004 | DeCharms | |
| 2005/0033154 A1 | 2/2005 | deCharms | |
| 2005/0154424 A1 | 7/2005 | Tass | |
| 2005/0197560 A1 | 9/2005 | Rao et al. | |
| 2005/0209512 A1 | 9/2005 | Heruth et al. | |
| 2005/0215884 A1 | 9/2005 | Greicius et al. | |
| 2005/0216071 A1 | 9/2005 | Devlin et al. | |
| 2005/0283053 A1 | 12/2005 | deCharms | |
| 2006/0155348 A1 | 7/2006 | deCharms | |
| 2006/0173259 A1 | 8/2006 | Flaherty | |
| 2006/0212090 A1 | 9/2006 | Lozano et al. | |
| 2006/0265022 A1 | 11/2006 | John et al. | |
| 2006/0276853 A1* | 12/2006 | Tass et al. | 607/45 |
| 2007/0067003 A1 | 3/2007 | Sanchez | |
| 2007/0123758 A1 | 5/2007 | Miesel et al. | |
| 2007/0142874 A1 | 6/2007 | John | |
| 2007/0191704 A1 | 8/2007 | deCharms | |
| 2007/0225674 A1 | 9/2007 | Molnar et al. | |
| 2007/0244407 A1 | 10/2007 | Osorio | |
| 2008/0001600 A1 | 1/2008 | deCharms | |
| 2008/0015459 A1 | 1/2008 | Llinas | |
| 2008/0045775 A1 | 2/2008 | Lozano | |
| 2008/0045853 A1* | 2/2008 | Gluckman et al. | 600/544 |
| 2008/0071150 A1 | 3/2008 | Miesel et al. | |
| 2008/0077039 A1 | 3/2008 | Donnett | |
| 2008/0243022 A1 | 10/2008 | Donnett | |
| 2008/0269631 A1 | 10/2008 | Denison et al. | |
| 2009/0082691 A1 | 3/2009 | Denison et al. | |
| 2009/0099623 A1 | 4/2009 | Bentwich | |
| 2009/0105521 A1 | 4/2009 | Bentwich | |
| 2009/0124919 A1 | 5/2009 | Ginosar et al. | |
| 2009/0163982 A1 | 6/2009 | deCharms | |
| 2009/0177144 A1 | 7/2009 | Masmanidis et al. | |
| 2009/0179642 A1 | 7/2009 | deCharms | |
| 2009/0192556 A1 | 7/2009 | Wu et al. | |
| 2009/0196471 A1 | 8/2009 | Goetz | |
| 2009/0220425 A1 | 9/2009 | Moxon | |
| 2009/0318794 A1 | 12/2009 | deCharms | |
| 2009/0318826 A1 | 12/2009 | Green et al. | |
| 2010/0069739 A1 | 3/2010 | deCharms | |
| 2010/0100153 A1 | 4/2010 | Carlson | |
| 2010/0114237 A1 | 5/2010 | Giftakis et al. | |
| 2010/0121213 A1 | 5/2010 | Giftakis et al. | |
| 2010/0121214 A1 | 5/2010 | Giftakis et al. | |
| 2010/0121215 A1 | 5/2010 | Giftakis | |
| 2010/0135553 A1 | 6/2010 | Joglekar | |
| 2010/0137937 A1 | 6/2010 | John et al. | |
| 2010/0241020 A1 | 9/2010 | Zaidel et al. | |
| 2010/0262205 A1 | 10/2010 | DeRidder | |
| 2010/0280334 A1 | 11/2010 | Carlson et al. | |
| 2010/0280335 A1 | 11/2010 | Carlson et al. | |
| 2010/0280336 A1 | 11/2010 | Giftakis et al. | |
| 2010/0280403 A1 | 11/2010 | Erdogmus | |
| 2010/0286748 A1 | 11/2010 | Midani | |
| 2011/0093045 A1* | 4/2011 | Moffitt | 607/59 |
| 2011/0105584 A1 | 5/2011 | Feinstein et al. | |
| 2011/0130797 A1 | 6/2011 | Talathi et al. | |
| 2011/0137371 A1 | 6/2011 | Giftakis et al. | |
| 2011/0144716 A1 | 6/2011 | Bikson et al. | |
| 2011/0184489 A1 | 7/2011 | Nicolelis et al. | |
| 2011/0196446 A1 | 8/2011 | Wu et al. | |
| 2011/0218454 A1 | 9/2011 | Low | |
| 2011/0257715 A1 | 10/2011 | Jarosh et al. | |
| 2011/0307029 A1 | 12/2011 | Hargrove | |
| 2012/0191157 A1 | 7/2012 | Stypulkowski et al. | |

OTHER PUBLICATIONS

Santaniello et al., "Adaptive Feedback Control in Deep Brain Stimulation: A Simulation Study", Proceedings of th4e 17th World Congress of the International Federation of Automatic Control, Jan. 1, 2008, pp. 11624-11629.

(PCTUS2012/0633539) PCT Notification of Transmittal of the International Search Report and the Written Opinion of the International Searching Authority, Mailed Sep. 25, 2012, 17 pages.

Loddenkkemper, et al., "Circadian Patterns of Pediatric Seizures," Neurology 76, Jan. 11, 2011: 145-153.

Eusebio, et al., "Resonance in Subthatamo-Cortical Circuits in Parkinson's Disease", Brain 2009, pp. 1-12.

Garrett et al., The Importance of Being Variable, The Journal of Neuroscience, Mar. 23, 2011, 31(12): 4496-4503.

Keimei et al., "Development Proposal: A Low Cost System for fMRI and Spectroscopic Screening and Monitoring of Alzheimer's Disease", Advanced Function Biomedical Imaging, University of Minnesota, Fall 2008, Dec. 12, 2008.

Lynall et al., "Functional Connectivity and Brain Networks in Schizophrenia", J. Neuroscience, Jul. 14, 2010—30(28):9477-9487.

Pihlajamaki et al., "Functional MRI Assessment of Task-Induced Deactivation of the Default Mode Network in Alzheimer's Disease and At-Risk Older Individuals," Behavioral Neurology 21 (1) (2009) 77-91.

Sperling, et al., "Functional Alterations in Memory Networks in Early Alzheimer's Disease," Neuromol Med (2010) 12:27-43.

Van Veen, et al., "Localization of Brain Electrical Activity via Linearly Constrained Minimum Variance Spatial Filtering" IEEE Transactions on Biomedical Engineering, vol. 44, No. 9, Sep. 1997.

Westlye, et al., "Increased Hippocampal Default Mode Synchronization During Rest in Middle-Aged and Elderly APOE ε4 Carriers: Relationships with Memory Performance," The Journal of Neuroscience, May 25, 2011, 31(21): 7775-7783.

* cited by examiner

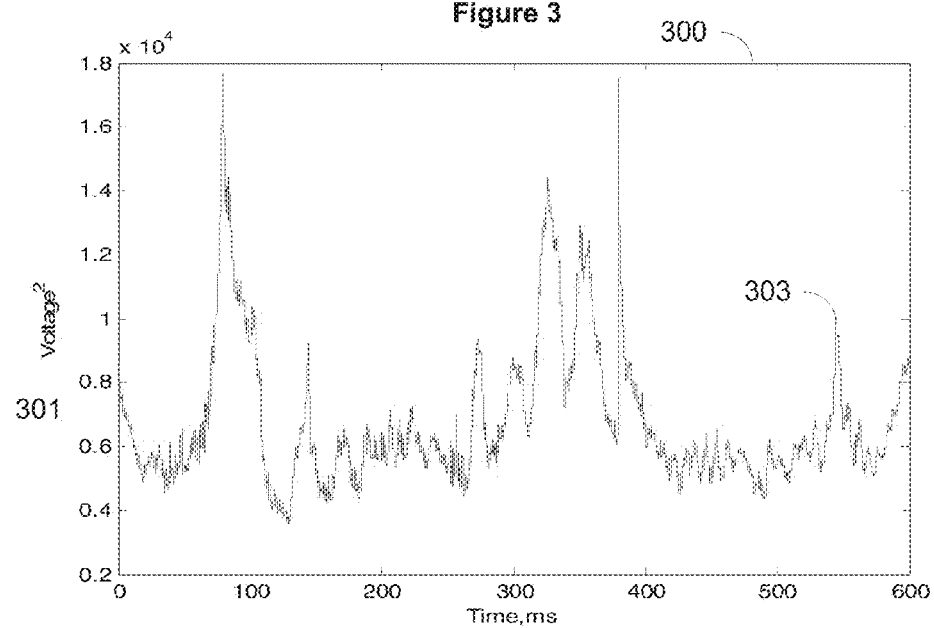
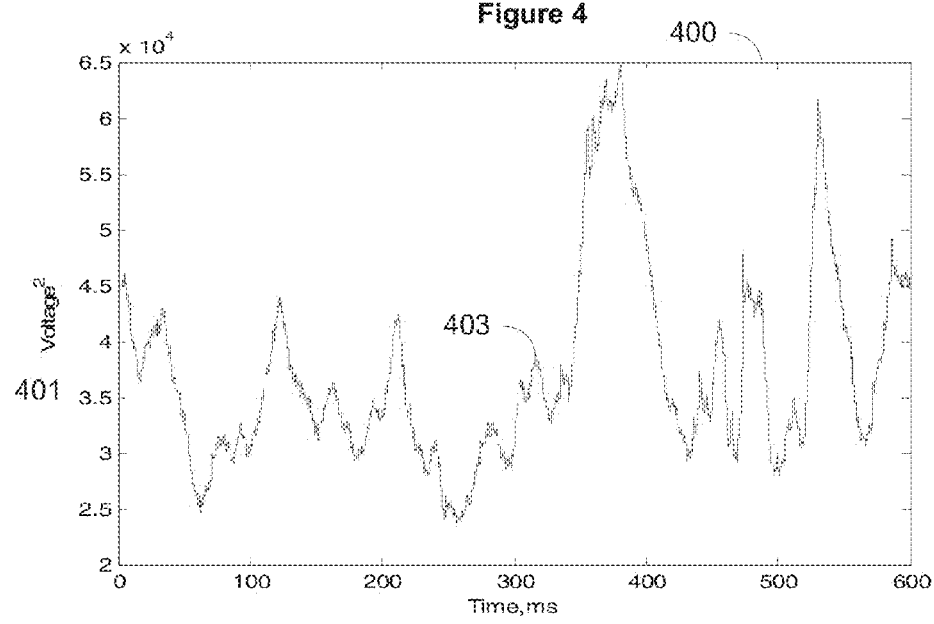

METHOD AND APPARATUS FOR ASSESSING NEURAL ACTIVATION

CROSS-REFERENCE TO RELATED APPLICATION

This application claims the benefit of priority of U.S. Provisional Patent Application No. 61/477,356, filed Apr. 20, 2011, the entire contents of which is incorporated herein by reference.

TECHNICAL FIELD

The disclosure relates to medical systems, and, more particularly, medical systems that track neural activation of a brain.

BACKGROUND

Implantable medical devices, such as electrical stimulation devices, may be used in different therapeutic applications, such as for deep brain stimulation, spinal cord stimulation, pelvic stimulation, gastric stimulation, peripheral nerve stimulation, or functional electrical stimulation of a target tissue site within a patient. An electrical stimulation device may be used to treat a variety of symptoms or conditions of a patient, such as chronic pain. In some therapy systems, an implantable electrical stimulator delivers electrical therapy to a target tissue site within a patient with the aid of one or more electrodes, which may be deployed by medical leads.

SUMMARY

In general, the disclosure relates to methods, systems, and devices for assessing neural activation and further controlling therapy based on the assessment of neural activation.

Various embodiments concern methods for assessing activation of a brain, comprising sensing one or more bioelectrical signals from one or more electrodes in contact with or proximate a brain, measuring the amplitude of the one or more bioelectrical signals over a period of time, calculating a plurality of variance values from the amplitude of the one or more bioelectrical signals, each of the variance values of the plurality corresponding to the variance of the amplitude for a different interval of time of a period of time with respect to the other variance values of the plurality of variance values, and assessing the relative level of neural activation of an area of the brain based on the plurality of variance values, wherein the area of the brain is assessed to have a relatively higher level of neural activation when the variance is relatively higher and the area of the brain is assessed to have a relatively lower level of neural activation when the variance is relatively lower and wherein sensing, measuring, calculating, and assessing are each performed at least in part by control circuitry. In some of the method embodiments, assessing the relative level of neural activation of the area of the brain comprises estimating the functional synaptic volume of the area of the brain. In some of the method embodiments, assessing the relative level of neural activation of the area of the brain comprises comparing the plurality of variance values and determining whether the variance has increased or decreased within the period of time, wherein the level of neural activation is assessed to have increased within the period of time if the variance increased and the level of neural activation is assessed to have decreased within the period of time if the variance decreased. In some of the method embodiments, assessing the relative level of neural activation comprising setting one or both of a variance baseline and a variance range based on at least some of the plurality of variance values, and determining whether one or more of the variance values deviate from one or both of the variance baseline and the variance range.

Some of the method embodiments further comprise tracking the effectiveness of a therapy based on the assessment of the relative level of neural activation of the area of the brain. In some cases, therapy is indicated to be at least somewhat effective if the variance of the amplitude of the one or more bioelectrical signals increases relative to a baseline variance associated with a lesser amount of the therapy or no therapy. Some embodiments further comprise titrating a drug therapy based on the assessment of the relative level of neural activation of the area of the brain. Some embodiments further comprise titrating an electrical stimulation therapy based on the assessment of the relative level of neural activation of the area of the brain.

Some of the method embodiments further comprise tracking a brain condition based on the assessment of the relative level of neural activation of the area of the brain, wherein the brain condition is one or both of an injury and a disease. Some of the method embodiments comprise determining the location of the one or more electrodes in the brain based on the assessment of the relative level of neural activation of the area of the brain. In some of the method embodiments, the one or more bioelectrical signals comprise local field potential signals.

Various embodiments concern a system comprising: a lead; one or more electrodes that are on the lead and are configured to sense bioelectrical activity; and control circuitry configured to sense one or more bioelectrical signals using the one or more electrodes, measure the amplitude of the one or more bioelectrical signals over a period of time, calculate a plurality of variance values from the amplitude of the one or more bioelectrical signals, each of the variance values of the plurality corresponding to the variance of the amplitude for a different interval of time of a period of time with respect to the other variance values of the plurality of variance values, and assess the relative level of neural activation of an area of a brain based on the plurality of variance values, wherein the area of the brain is assessed to have a relatively higher level of neural activation when the variance is relatively higher and the area of the brain is assessed to have a relatively lower level of neural activation when the variance is relatively lower.

In some embodiments, the control circuitry is configured to assess the relative level of neural activation of the area of the brain by estimating the functional synaptic volume of the area of the brain. In some embodiments, the control circuitry is configured to assess the relative level of neural activation of the area of the brain by comparing the plurality of variance values and determining whether the variance has increased or decreased within the period of time, wherein the level of neural activation is assessed to have increased within the period of time if the variance increased and the level of neural activation is assessed to have decreased within the period of time if the variance decreased. In some embodiments, the control circuitry is configured to assess the relative level of neural activation of the area of the brain by setting one or both of a variance baseline and a variance range based on at least some of the plurality of variance values, and determining whether one or more of the variance values deviate from one or both of the variance baseline and the variance range. In some embodiments, the control circuitry is configured to track the effectiveness of a therapy based on the assessment of the relative level of neural activation of the area of the brain.

In some embodiments, the control circuitry is configured to track a brain condition based on the assessment of the relative level of neural activation of the area of the brain and provide an output on a display based on the tracking of the brain condition, wherein the brain condition is one or both of an injury and a disease.

In some embodiments, therapy is indicated to be at least somewhat effective if the variance of the amplitude of the one or more signals increases relative to a baseline variance associated with a lesser amount of the therapy or no therapy. In some embodiments, the control circuitry is configured to titrate a drug therapy based on the assessment of the relative level of neural activation of the area of the brain. In some embodiments, the control circuitry is configured to titrate an electrical stimulation therapy based on the assessment of the relative level of neural activation of the area of the brain.

In some embodiments, the control circuitry is configured to determine the location of the one or more electrodes in the brain based on the assessment of the relative level of neural activation of the area of the brain and indicate the location on a display. In some cases, the one or more signals comprise local potential signals.

Various embodiments concern a system for assessing activation of a brain, comprising means for sensing one or more bioelectrical signals from a brain; means for measuring the amplitude of the one or more bioelectrical signals over a period of time, means for calculating a plurality of variance values from the amplitude of the one or more bioelectrical signals, each of the variance values of the plurality corresponding to the variance of the amplitude for a different interval of time of a period of time with respect to the other variance values of the plurality of variance values, and means for assessing the relative level of neural activation of an area of the brain based on the plurality of variance values, wherein the area of the brain is assessed to have a relatively higher level of neural activation when the variance is relatively higher and the area of the brain is assessed to have a relatively lower level of neural activation when the variance is relatively lower.

Various embodiments concern a physically embodied computer-readable medium comprising processor executable program instructions that, when executed by the processor, cause a medical device to: sense one or more bioelectrical signals from a brain; measure the amplitude of the one or more bioelectrical signals over a period of time; calculate a plurality of variance values from the amplitude of the one or more bioelectrical signals, each of the variance values of the plurality corresponding to the variance of the amplitude for a different interval of time of a period of time with respect to the other variance values of the plurality of variance values; and assess the relative level of neural activation of an area of the brain based on the plurality of variance values, wherein the area of the brain is assessed to have a relatively higher level of neural activation when the variance is relatively higher and the area of the brain is assessed to have a relatively lower level of neural activation when the variance is relatively lower.

The details of one or more examples are set forth in the accompanying drawings and the description below. Other features, objects, and advantages will be apparent from the description and drawings, and from the claims.

BRIEF DESCRIPTION OF DRAWINGS

FIG. 3 is a plot of brain signal variance for a patient off medication.

FIG. 4 is a plot of brain signal variance for a patient on medication.

DETAILED DESCRIPTION

Figure 1:
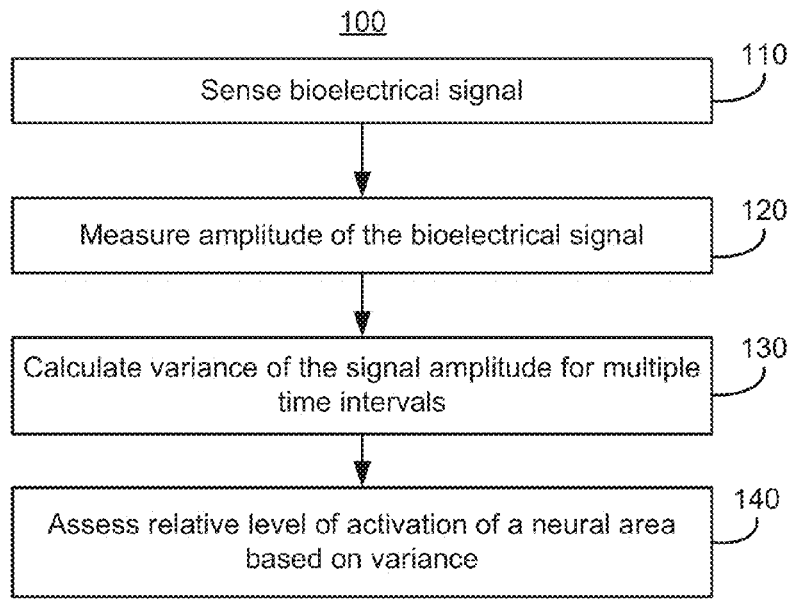
FIG. 1 is a flow diagram for assessing levels of neural activation.

The human brain is composed of billions of neurons electrically interconnected and organized into various areas to perform a variety of functions. The neurons of a particular area can be associated with one or more different brain functions. These areas can overlap and share networks of neurons. The electrical activation of neurons is responsible for the function of the brain and communication amongst the various areas of the brain along networks. It is generally thought that the activation of numerous neurons is necessary to carryout each brain function. Moreover, for various areas of the brain, many of the neurons in one or more areas of the brain will depolarize, sometimes in synchrony, in an effort to carryout a function supported by the one or more areas. The activation of neurons can be measured as a bioelectrical signal, such as a local field potential (LFP), electroencephalogram (EEG), magnetoencephalography (MEG), and/or electrocorticogram (ECoG) signal, among other measurement techniques.

Certain neurological and psychiatric disorders, as well as brain injuries, can be characterized by deficits in large-scale integration across distributed brain networks. Subsequent to a variety of neurological injuries (e.g., stroke) and diseases (e.g., Parkinson's disease) the normal patterns of neuronal activity can be disrupted, possibility in multiple brain regions, due to cell degeneration and death of neurons or other consequences of injury and disease. Such damage can weaken whole areas of the brain and inhibit brain areas in properly carrying out their various functions. Moreover, damage from disease or injury can weaken the connections between brain areas and compromise the ability of brain networks to communicate and coordinate.

As a consequence of injury or disease, a decrease in the number of activating neurons in a brain area may be experienced. For example, some of the neurons of a damaged brain area may activate infrequently, as compared to their normally healthy state, or not activate at all. In some brain conditions, certain areas of the brain can become overactive or otherwise operate in a manner that interferes with other brain areas and is detrimental to proper brain function.

Various therapies can be administered to raise the activity levels of neurons and thereby attempt to correct inadequate neural activation. Some therapies can lower or suppress the activation of overactive or problematic brain areas. However, determining the relative amount of activating neurons can be difficult. For example, determining an exact number of activating neurons in a brain area is exceedingly difficult if not impossible. Each activation of a neuron creates an electrical dipole having a magnitude and a direction. The neurons of each brain area are arranged in unpredictable orientations, and generally not in uniform directions. Therefore, an LFP signal measured from within the brain area (e.g., using an electrode located within the brain area) will usually be an erratic signal as the numerous neurons in different directions and orientations with respect to the electrode (and each other) depolarize at various times. Furthermore, the LFP signal will usually sum to zero over time because the positive and negative voltage measurements will tend to cancel each other out. As such, signal magnitude alone may not be an adequate tool for determining the relative amount of neurons activating in a brain area because lesser neural activation can appear the same as greater neural activation because of dipole canceling.

This disclosure concerns methods and devices for characterizing activation of one or more brain areas. In various embodiments, a brain condition is tracked and/or a therapy titrated based on brain activation levels over time. Various methods and devices of the present disclosure determine the relative level of neural activation of a brain area based on the variation in a bioelectrical signal over time. The variation in the bioelectrical signal over time can be indicative of the number of neurons activating because of the unpredictable arrangement and activation patterns of the neurons of the brain area. The neurons surrounding an electrode will be arranged in many different orientations relative to the electrode and may not follow a predictable pattern. The activation of each neuron can therefore cause a positive or negative change in amplitude of a LFP measured from the electrode, causing a seemingly erratic pattern as the LFP signal frequently jumps to positive and negative measurements depending on which neurons are activating, and where the neurons are located. The inventors of the subject matter of the present disclosure have demonstrated that the variance of the LFP signal is indicative of the number of neurons activating because each activating neuron adds another possible positive or negative amplitude deflection to the LFP signal. As such, the greater the variation observed, the greater number of neurons influencing the LFP signal, even if the dipoles tend to cancel over time. Snapshots of variation corresponding to different intervals of time can be compared to one another to determine whether the variation, from which the level of neural activation of the neurons can be inferred, is increasing, decreasing, or staying the same between the different internals of time. FIG. 1 demonstrates various aspects of the present disclosure.

FIG. 1 illustrates a flow diagram of a method 100 for assessing activation of a brain area. The method 100 includes sensing 110 a bioelectrical signal. Sensing 110 can include receiving one or more signals from the brain, such as EEG, ECoG, MEG, and/or LFP signals via sensing circuitry. The method 100 further includes measuring 120 the amplitude of the bioelectrical signal in the time domain. Measuring 120 may be performed by circuitry of an implantable medical device (IMD) and/or external device, for example. The measured 120 amplitude values may be stored in memory. Multiple time domain variance values can be calculated 130 based on the measured 120 amplitude values of different time intervals. Each time interval may be, for example, five seconds. The time intervals may overlap to share some, but not all, amplitude values, or the time intervals may concern entirely different periods of time (e.g., adjacent or separated in time).

The relative level of neural activation of a neurological area, such as an area of a brain, can be assessed 140 based on the calculated 130 variance over time. As discussed herein, the variance of a bioelectrical signal, such as the variance of the amplitude of a LFP signal, is proportional to the number of neurons activated in a brain area. The variance is calculated 130 for two or more time intervals and a comparison is made as part of the assessment 140 to, among other things, determine whether the variance is changing over time. Sensing 110, measuring 120, calculating 130, and assessing 140 may be performed automatically by circuitry of a medical device that may provide outputs (e.g., displaying of an indicator of activation or a change in therapy) based on the assessment 140. "Activation level' or "level of neural activation", as the terms are used herein, refer to the amount of neural depolarization in a given area, such as a brain area. While the exact number of neurons depolarizing in a brain area cannot be determined, the present disclosure concerns determining the relative amount of neurons activating by some measure and comparing the relative amount across different states and times to determine whether the level of neural activation is changing (e.g., increasing or decreasing) across the different states and times.

In some cases, LFP variance can be used to estimate the number of activated synapses within a volume of tissue as an estimate of the functional synaptic volume of the tissue. Based on a proportional relationship between the number of neurons activating proximate an electrode and the LFP variance, the variance can be used to estimate the number of functioning synapses influencing the LFP measurements.

Figure 2:
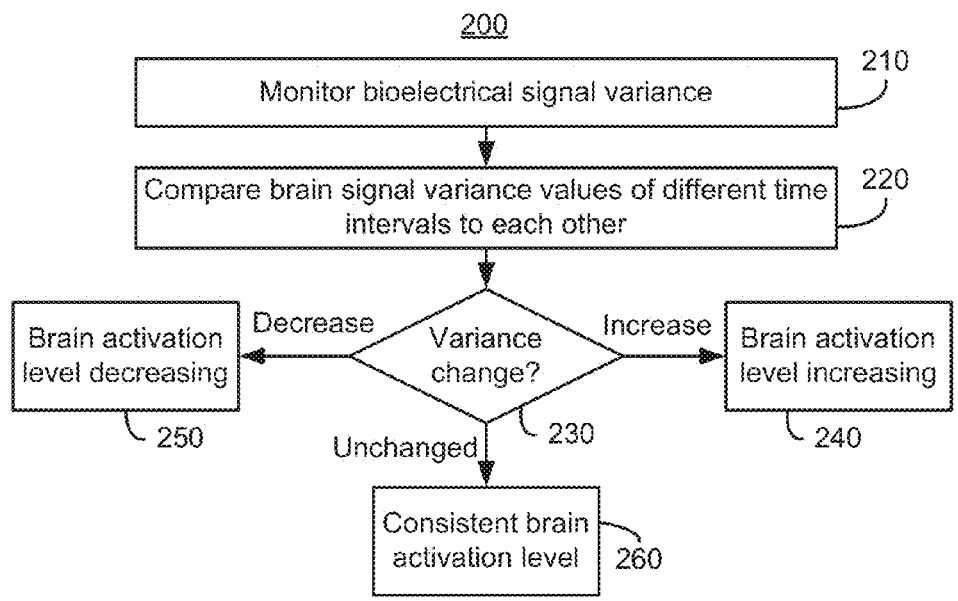
FIG. 2 is a flow diagram for identifying changing levels of neural activation.

FIG. 2 illustrates a flow diagram of a method 200 for determining whether brain activation is increasing or decreasing over time. The method 200 includes monitoring 210 bioelectrical signal variance. Monitoring 210 bioelectrical signal variance may be performed in any manner referenced herein, including by sensing 110 a bioelectrical signal, measuring 120 the bioelectrical signal, and calculating 130 variance for multiple time intervals in the manner of FIG. 1.

Variance values corresponding to different intervals in time can be calculated and stored in memory as part of monitoring 210. A first variance value can be calculated from a LFP signal sensed during a first interval of time and a second variance value can be calculated from a LFP signal sensed during a second interval of time, where the first interval of time is before the second interval of time. The different time intervals may correspond to different therapy configurations or patient states. For example, therapy may not be administered in association with the first time interval (e.g., no drugs or electrical stimulation is administered proximately before and/or during the first time interval) while therapy is delivered during and/or immediately preceding the second time interval. The different time intervals can then represent therapy-off and therapy-on configurations, which can later be compared. Alternatively, the first time interval may correspond to a resting patient state while the second time interval corresponds to an active patient state, or other change in patient state. The different time internals can correspond to any change in patient state or therapy configuration, although in some cases no specific change in patient state or therapy configuration is anticipated or attempted and the different time intervals just test the neural activations levels over time.

While a first time interval and a second time interval are used herein for simplicity in describing FIG. 2, it is noted that this and other embodiments can utilize two or more time intervals, such as ten, one hundred, or a thousand time intervals. Likewise, multiple therapy configurations and/or patient states can be tested across multiple time intervals, such as incrementally increasing a therapy amplitude or drug concentration for each time interval of a plurality of time intervals. In various embodiments, different time intervals may be overlapping but not matching time interval, sequential and contiguous time intervals, or sequential non-contiguous time intervals. In this manner, a time period may comprise multiple different intervals.

Variance values for different periods of time can be compared 220 to each other. Such comparison 220 may include a processor of control circuitry determining which of two or more variance values is greater. Comparison 220 may also include plotting the variance values over time on a chart. Based on the comparison 220 of variance values, it can be determined whether the variance in the bioelectrical signal is changing 230 over time.

For example, based on the comparison 220, it can be determined whether a first variance value calculated from a first time interval is less than, greater than, or equal to a second variance value calculated from a second time interval, wherein the second time interval is after the first time interval. If the second variance value is greater than the first variance value, then the variance has increased between the two time intervals. If the second variance value is less than the first variance value, then the variance has decreased between the two time intervals. If the second variance value is the same or similar (within a margin) than the first variance value, then the variance has not changed between the two time intervals.

As discussed herein, relative changes in the level of brain area activation can be inferred from changes in variance proportionally. Therefore, if the variance of the bioelectrical signal amplitude increases between the first and second time intervals, then it can be concluded that the brain activation level increased 240 between these two time intervals. If the variance of the bioelectrical signal amplitude decreases between the first and second time intervals, then it can be concluded that the brain activation level decreased 250 between these two time intervals. If the variance of the bioelectrical signal amplitude is unchanged between the first and second time intervals, then it can be concluded that the brain activation level was consistent 260.

A brain condition, such as a condition relating to an injury or disease, can be tracked by comparing variance values of different time intervals of a period. In such cases, the time intervals may represent different sampled times for determining whether a disease or injury condition is improving or worsening based on increasing, decreasing, or unchanging amounts of brain activation between the different time intervals. For example, in a disease or injury condition characterized by abnormally low neural activation, if the first time interval is before a second time interval, then an increase in variance from the first time interval to the second time interval may indicate that the brain condition is improving based on increased neural activation 240 in the brain area being monitored 210. Likewise, a decrease in variance may indicate that the brain condition is worsening based on decreased neuron activation 240 in the brain area being monitored 210. These examples, however, assume that greater neural activity is indicative of a healthier condition. In other cases, particularly relating to conditions associated with overactive brain areas, decreasing 250 brain activation can indicate an improving patient condition while increasing 240 brain activation can indicate a worsening patient condition. An unchanged variance may indicate that the brain activation level is consistent 260 between the different time intervals, and therefore that the brain condition is unchanged as it relates to the number of neurons activating. In various embodiments of tracking a brain condition, a therapy may be delivered in none, some, or all of the time intervals.

Furthermore, a patient condition can be tracked to be worsening if lesser levels of neural activation over time are inferred through decreasing variance over time, in the case that neural activation levels should be staying consistent or increasing. In such cases, a patient condition can be tracked to be improving if greater levels of activation over time are observed through increasing variance over time. In the case of an Alzheimer's disease patient, decreasing variance over time may indicate that the patient's cognitive capacity is decreasing. Outputs can be generated based on increasing, decreasing, and unchanging variance over time. For example, a processor of control circuitry may cause an indication of increasing neural activity, decreasing neural activity, or unchanging neural activity to be displayed or printed. A processor could likewise cause an indication of increasing, decreasing, or unchanging variance over time to be displayed or printed. In this way, a computer performing the processes referenced herein may assess variance data and indicate that a brain condition is worsening based on decreasing levels of activation of one or more brain areas based on input data (e.g., LFP amplitude data covering a time period of six months). Based on variance calculations, such a computing system may also suggest, initiate, and/or modify a therapy.

Conclusions can be made about how brain activation levels are influenced by various factors based on whether the variance is changing 230 between different time intervals. In some cases, the first and second intervals correspond to different patient states or activity levels (e.g., awake vs. asleep or resting vs. active). Comparisons between the variance levels of the different intervals can then indicate whether neural activation is different between these states (e.g., higher or lower in resting vs. active states, or higher or lower in therapy-on vs. therapy-off configurations).

In some embodiments, the different states can be different therapy configurations. For example, if the first time interval was a therapy-off interval and the second time interval was a therapy-on interval, then the change in variance between these time intervals may indicate that the therapy increased the level of brain activity for the brain area being monitored 210. In some cases, both of first and second time intervals can be periods in which therapy was delivered, but where different therapy parameters were used so as to determine whether the variance is changing 230 between the administration of different therapy parameters for the different intervals. In the case of a consistent 260 brain activation level, it may be concluded that any controlled changes between the first and second time periods (e.g., use of therapy or a change in therapy parameter) had no effect.

The steps of FIG. 2 as described herein may be performed automatically by control circuitry of a medical device. For example, a medical device may monitor 210, compare 220, assess variance changes 230, and determine that neural activation of a brain area is increasing 240, decreasing 250, or remaining consistent 260, as well as perform the other functions described herein.

In some embodiments, the level of neural activation of a brain area may be assessed by sensing multiple bioelectrical signals from multiple locations of a brain, at least one of the areas not being associated with a brain condition (e.g., not suspected of being impaired or otherwise abnormal as confirmed by fMRI and/or the absence of symptoms associated with impairment of the brain area). The variance values of the signals from the different brain areas can be compared to one another. For example, a ratio can be determined based on the variance of a first area and the variance of a second area, wherein the first area is known to be healthy and the second area is suspected of being in an impaired condition by injury or disease. An imbalance in the ratio may indicate that the second brain area is electrically under-active or over-activate, depending on if the second brain area shows less variance or greater variance relative to the first brain area. The amount of the imbalance may indicate the degree to which the second brain area is under-active or over-active. The variance ratio of first and second brain areas can also be compared to a variance ratio of similar first and second brain areas of another subject or population data to determine whether ratio imbalances between the two areas are normal or abnormal.

FIGS. 3-4 illustrate plots of LFP signal variance over time for a Parkinson's disease patient. The patient is off-medication in the case of FIG. 3 and on-medication in the case of FIG. 4. The plot 300 of FIG. 3 includes variance 301 ordinate axis in units of voltage squared and a time 302 abscissa axis in units of milliseconds. The variance trace 303 indicates the calculated LFP variance 301 value over time 302. As shown in FIG. 3, the variance is generally in the range of 0.4 to 1.8 volts squared, with an average around 0.5 to 1.0 volts squared.

The plot 400 of FIG. 4 includes variance 401 ordinate axis in units of voltage squared and a time 402 abscissa axis in units of milliseconds. The variance trace 403 indicates the calculated LFP variance 401 value over time 402. As shown in FIG. 4, the variance is generally in the range of 2.5 to 6.5 volts squared, with an average around 3.0 to 4.5 volts squared.

A comparison between the variance values of therapy-off and therapy-on states shows a relatively dramatic difference in values. A comparison between the variance levels of FIGS. 3 and 4 indicate that the variance is greater in FIG. 4, corresponding to a therapy-on state, as compared to FIG. 3, corresponding to a therapy-off state. In particular, the therapy-on variance in FIG. 4 appears to be about 6 times greater than the therapy-off variance in FIG. 3.

Based on the differences in variance, it can be concluded that greater neuron activation was observed in the time 402 interval of FIG. 4 as compared to the time 302 interval of FIG. 3. Furthermore, being that the second time 402 interval is associated with drug administration and the first 302 time period is not, it can be determined that the drug facilitated an increase in activation of neurons of a brain area, which is generally associated with a healthier brain condition for this condition. As such, the magnitude of amplitude variance over time can be used for characterizing the relative level of neural activation of neurons in a brain area and can further guide administration of therapy, such as identifying one or more effective therapies and titrating therapy.

Figure 5:
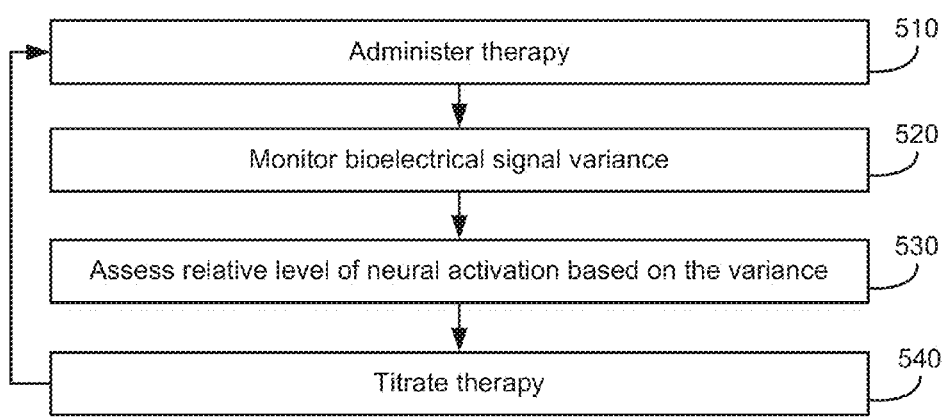
FIG. 5 is a flow diagram for titrating therapy based on neural activation.

FIG. 5 illustrates a flow diagram of a method 500 for titrating therapy. The method 500 includes administering 510 a therapy. Administration 510 of the therapy can include any type of therapy administration, including but not limited to delivering electrical stimulation or prescribing or delivering a drug. The method 500 also includes monitoring 520 variance of a bioelectrical signal, which can be done in any manner, including using the techniques of FIGS. 1 and 2 or otherwise referenced herein. Based on the monitored 520 bioelectrical signal variance, the relative level of neural activation can be assessed 530. Such assessment 530 can be performed in any manner, including in the manner of FIG. 2 or otherwise referenced herein. The assessment 530 may determine, for example, that neurological activity of a particular brain area is decreasing or decreasing. The assessment 530 may also include determining whether the change in neurological activity is appropriate or intended (e.g., determine whether the increase or decrease represents an improvement or worsening of the patient condition, which depends on the patient's particular disease or injury condition).

The therapy can be titrated 540 based on the assessed 530 relative level of the brain activation. For example, the assessment 530 can determine whether the brain activation level, as measured by variance, is at a target level of brain activation. A target level (or target range) can be predetermined from what level of neural activation is normally seen in a healthy individual based on clinical or population data or is set by a clinician for a particular patient. Therapy titration 540 may comprise initiating a therapy which was not delivered before, increasing the intensity of the therapy, decreasing the intensity of the therapy, and/or in some manner changing the administration 510 of the therapy to change its effect. The intensity of a therapy may be increased by increasing the amount of a drug, increasing the potency of the drug, increasing the concentration of a drug, and/or increasing the frequency with which the drug is taken/delivered, among other options. In the case of an electrical stimulation therapy, the intensity of an electrical stimulation may be increased by increasing the amplitude, duration, and/or frequency of delivery. The intensity of the therapy may likewise be decreased in the opposite manner.

In various embodiments, the therapy may be titrated 540 to increase the intensity in the case that brain activity is assessed 530 to be decreasing over time. The therapy may be titrated 540 to decrease the intensity in the ease that brain activity is assessed 530 to be increasing over time. While these examples refer to disease or injury states that may manifest as lowered brain activity, the therapy may be titrated 540 conversely in the case that the disease or injury manifests as elevated brain activation levels (e.g., increasing therapy intensity when activity increases to lower the activation level).

It is noted that the steps of the method 500 of FIG. 5 (as well as the steps of other procedures referenced herein) can be performed sequentially or concurrently. For example, therapy may sometimes or always be administered 510, bioelectrical signal variance may sometimes or always be monitored 520, brain activation levels may sometimes or always be assessed 530, and/or therapy may sometimes or always be adjusted as needed through titration 540. Administration 510, monitoring 520, assessing 530, and titrating 540 may be performed automatically by control circuitry of a medical device, as discussed herein.

Figure 6:
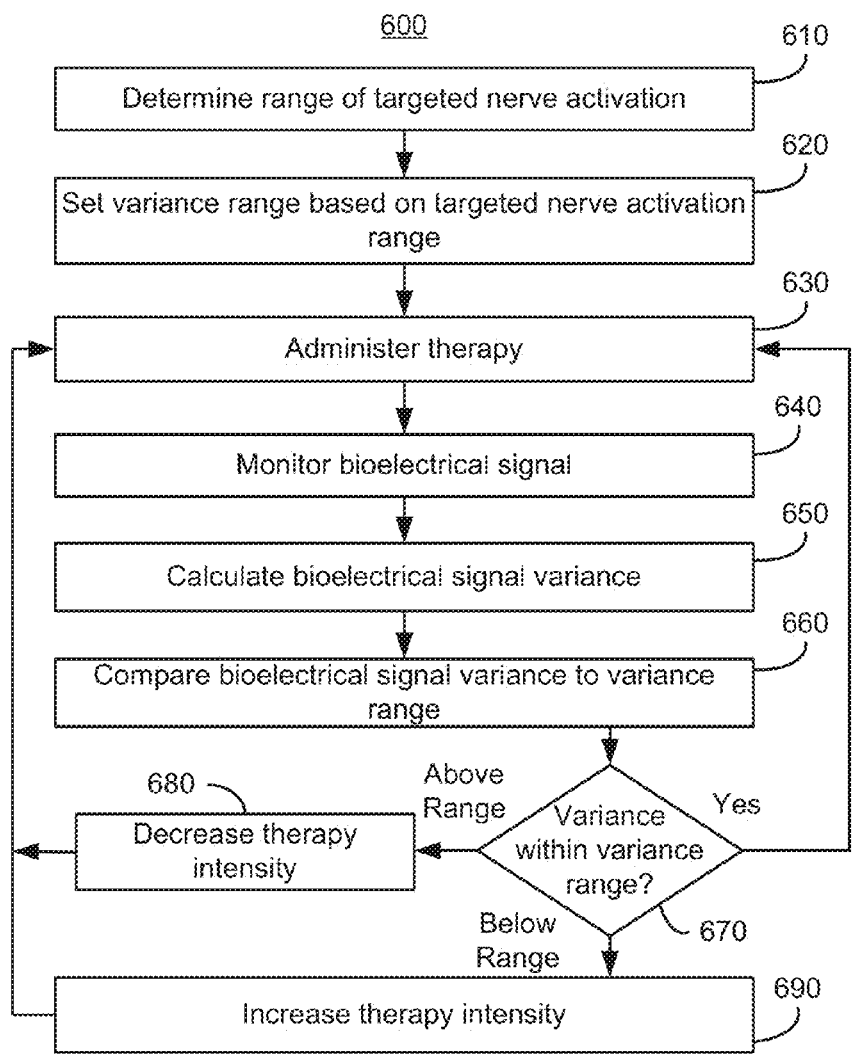
FIG. 6 is a flow diagram for changing therapy parameters based on neural activation.

FIG. 6 illustrates a flow diagram of a method 600 for adjusting therapy parameters. The method 600 includes determining 610 a range of targeted neural activation. A range of targeted neural activation may be the range of neural activation for a certain area of the brain usually observed in healthy individuals. The range may be set by a clinician for a particular patient. The range may be based on clinical or population data. In some cases, a patient may go through a fMRI procedure to assess levels of brain activation. The levels of brain activation as determined by fMRI may be compared to fMRI data from clinical or population data to determine the degree to which a patient has underactive, overactive, or normal neural activity for an area of the brain. The results of an fMRI may be normalized or in some manner quantified as an objective measure of the level of neural activation. A range may then be determined 610 based on the objective measure or comparison to clinical or population data for what the patient's brain activation levels should be. In some cases, an absolute variance value can facilitate comparison to variance information from other patients to assess the relative brain condition of a subject.

A variance range may be set 620 based on the targeted neural activation range. In this way, the range of targeted neural activation may be measured in terms of the same units of measurement of variance (e.g., voltage squared). The range may be, for example, 3-7 volts squared. In some cases, the variance range may initially be set 620 with the step of determining 610 the range of targeted neural activation. In some embodiments, a targeted range of neural activation and/or variance range may be preprogrammed into a device, such as an implantable brain stimulation device having closed loop operation using the preprogrammed targeted range of neural activation as measured by variation and/or another range.

Continuing with the example of using fMRI, the results of the fMRI procedure may be used to set 620 the variance range. In various cases, fMRI procedure may show the degree to which the patient has abnormally low or high neural activation levels for a particular brain area. For example, fMRI may show that the patient is only slightly below a normal range of activation based on population data and a variance range may accordingly be set 620 to bring about only a slight increase in variance corresponding to a slightly higher activation level. In other cases, larger increases or decreases in activation levels, and accordingly larger increases or decreases in variance of a bioelectrical measure, may be desired based on a comparison of the patient's fMRI activation results to population data. In various embodiments, once a range of targeted neural activation is determined 610, the variance range can be set 620 by determining the current variance of a bioelectrical and how far the patient is off from normal or acceptable neural activation levels. For example, continuing with the above example of using fMRI to determine that a patient has only slightly depressed levels of neural activation, the determined 620 targeted neural activation range may be set only slightly higher than what as observed by fMRI. The variance of a bioelectrical signal may also be calculated to determine the untreated relative brain activation level of the patient, and the variance range may be set 620 as only slightly higher than the calculated variance value consistent with the difference between the fMRI observation and the determined 620 neural activation range targeted.

A scalar table or plot can be referenced to set 620 a variance range. For example, being that variance and neural activity are proportional, if a 20% increasing in neural activation is determined 610 to be targeted based on fMRI data, then a predetermined chart or plot can be referenced to associate the 20% increase with a variance change. In some embodiments, the target neural activation range may be determined 610, and later adjusted, based on outward manifestations of disease or injury. Likewise, the variance range may be set 620 and later adjusted based on outward manifestations of disease or injury.

Therapy may be administered 630 in any manner described herein, including electrical stimulation and/or drug prescription or delivery. The administered 630 therapy will generally be therapy that has the capability of directly or indirectly changing the neural activation level of the targeted area for which the variance range was set 620.

The method 600 includes monitoring 640 a bioelectrical signal, which can include any monitoring technique referenced herein. For example, the signal may be a LFP signal sensed using one or more electrodes located within the tissue targeted for therapeutic change in level of neural activation. Variance values can be calculated 650 based on the monitored 640 bioelectrical signal. The variance values can be compared to the previously set 620 variance range to determine whether the variance is within the variance range 670. If the calculated 650 variance is below the variance range, which can indicate that the brain area is activating at a tower level than the determined 610 range of targeted neural activation, then the therapy intensity can be increased 690 and the method 600 can loop back to repeat steps with updated therapy parameters.

If the therapy is a drug therapy, then increasing 690 the therapy intensity can include increasing a dosage, potency, concentration, frequency of delivery, or other aspect that can make the therapy administration 630 more impactful. If the therapy is an electrical stimulation therapy; then increasing 690 the therapy intensity can include increasing an energy parameter (e.g., amplitude, pulse width, frequency of pulses, and/or duration of delivery), or other aspect that can make the therapy more impactful. For example, pulse energy may be increased or decreased by changing the pulse width. In some cases, stimulation electrodes can be changed in an attempt to increase 690 therapy intensity by scanning through various electrode combinations as the method 600 loop repeats until a satisfactory electrode combination is identified that can cause brain activation levels, as measured by bioelectrical signal variance, to change as desired.

If the calculated 650 variance is above the variance range 670, which can indicate that the brain area is activating at a higher level than the determined 610 range of targeted neural activation, then the therapy intensity can be decreased 680. A therapy intensity decrease 680 may be performed in a comparable manner to therapy intensity increase 690, such as decreasing a dosage, concentration, delivery frequency, and/or amount of a drug or decreasing the frequency, amplitude, pulse width, and/or duration of electrical stimulation.

If the calculated 650 variance is within the variance range 670, which can indicate that the brain area is activating within the determined 610 range of targeted neural activation, then the therapy intensity can remain unchanged and the method 600 can continue in loop fashion to perform another variance range check.

In some embodiments, the therapy is administered 630 to suppress brain activity, such as an overactive area of the brain causing seizures, interfering with other brain areas, inappropriately suppressing other brain areas, or causing other problems. The method 600 can be modified to account for the desire to decrease, rather than increase, neuron activity in the brain area. For example, if the calculated 650 variance is above the variance range 670, which can indicate that the brain area is activating at a higher level than the determined 610 range of targeted neural activation, then the therapy intensity can be increased to further suppress the overactive brain area. If the calculated 650 variance is below the variance range 670, which can indicate that the brain area is activating at a lower level than the determined 610 range of targeted neural activation, then the therapy intensity can be decreased to ease suppression of the brain area.

In various embodiments, instead of a range for targeted neural activation being determined 610, a level is determined 610, such as a threshold corresponding to the minimum (or in some cases maximum) amount of neural activation desired. Likewise, a variance threshold can be set 620 instead of setting 620 a variance range. The method 600 may then be modified to increase 690 therapy intensity when the calculated variance 650 is below the variance threshold and/or decrease 680 therapy intensity when the calculated variance 650 is above the variance threshold, in embodiments where the therapy aim is to promote neuron activation in the brain area. In the case of a maximum variance threshold, such as when the therapy is attempting to suppress brain activity, the therapy intensity may be increased 690 when the calculated variance 650 is below the variance threshold and/or decrease 680 therapy intensity when the calculated variance 650 is above the variance threshold.

As demonstrated in FIG. 6, the steps of the method 600 can cycle to scan through various parameters, such as incrementally increasing a pulse voltage of the electrical stimulation until an efficacious amplitude is found. By scanning through the various parameters, the minimum amount of drug or stimulation energy needed to achieve the targeted neural activation range or level can be determined and updated. As such, the techniques of the method 600 of FIG. 6, as well as the method 500 of FIG. 5 and in the other embodiments referenced herein, can scan therapy parameters to identify appropriate parameters that provide for efficacious therapy. In some cases, an electrode on a lead may be advanced or retracted within the brain as a parameter until an optimal electrode position is found for achieving the determined 610 neural activation target range. Electrodes or electrode combinations for delivering electrical stimulation can also be changed until a satisfactory electrode combination is found for achieving the determined 610 neural activation target range.

Although the flow diagram of FIG. 6 illustrates administering 630 therapy, monitoring 640 a bioelectrical signal, calculating 650 variance, and comparing 660 as sequential steps of a loop, these and other steps of the method 600 may be performed concurrently or in a different order. For example, administering 630 therapy, monitoring 640 a bioelectrical signal, calculating 650 variance, and comparing 660 could always be performed, or certain steps such as comparing 660 may only be performed periodically according to a schedule. In some embodiments, blanking in sensing or stimulation can be used to allow sensing of bioelectrical signals without concurrent electrical stimulation delivery.

In some embodiments, the variance of a bioelectrical signal may be used to trigger a therapy or turn therapy off. A variance threshold can be developed for a particular patient to trigger therapy or turn therapy off. For example, therapy may only be administered when brain neuron activation levels fall below a certain level based on variance falling below a threshold level. In various embodiments, therapy may only be administered when neural activation levels rise above a certain level in the case of therapy to suppress activation. The brain activation level may be set as a variance level that corresponds with the brain activation level (e.g., based on clinical or population date) beyond which therapy is needed. For example, in the case of electrical stimulation or drug delivery to support activation of neurons in a brain area, the electrical stimulation or drug can be delivered when the variance falls below a threshold set as the minimum activation level. In the case of electrical stimulation or drug delivery to suppress activation of neurons in a brain area, the electrical stimulation can be delivered when the variance rises above a threshold set as the maximum activation level.

A variance threshold or range can be determined by monitoring a bioelectrical signal of a patient when the patient is in a preferable state, such as when relief from Parkinson's disease systems are experienced, which can be self reported or observed subjectively by a clinician or objectively by devices such as an accelerometer. A variance value can be calculated for the bioelectrical signal data that is temporally correlated with the preferable state. A preferable state may also be identified by fMRI or other imaging technique able to characterize activation of various areas of the brain, such as temporally correlating variance values with activation of a particular brain area as shown by an fMRI. The variance value can then serve as the variance threshold, above or below which therapy can be triggered. The setting of a variance threshold can facilitate an automated triggering of therapy, such as by a processor of control circuitry determining that a current variance value exceeds a variance threshold and therefore triggering therapy delivery.

In some embodiments, a targeted neural activation range or baseline may be determined by determining activation levels via fMRI, LFP variance as disclosed herein, or other technique based on a patient indication of a preferred condition. For example, when a Parkinson's disease patient thinks that he or she is currently has minimal symptoms (e.g., tremor), or an Alzheimer's patient thinks that he or she currently has a clearer mind, then the patient or clinician can provide an input (e.g., pushes a button on a control) and a device can start sensing, saving, and/or analyzing data to determine the targeted neural activation range as measured by variance (i.e. the level sensed during this preferred patient state). The targeted neural activation range as measured by variance can correspond to the ranges sensed at the time of the input. The method 600 can then adjust therapy as described herein to promote the brain state where the patient experienced minimal symptoms.

In various embodiments, variances values of a bioelectrical signal may indicate proximity of the electrode(s) used in sensing to a particular brain area. For example, certain areas of the brain are known to be more active as compared to other brain areas. An electrode on a lead may be advanced in the brain while sensing a LFP signal is performed using the electrode. As the electrode nears a particular landmark in the brain, if the landmark is associated with high levels of neural activation, then a variance parameter may increase as the electrode gets closer to the landmark. Moreover, variance patterns may be established for one or more brain areas, and those brain areas may subsequently be identified based on sensed variance patterns matching one or more of the established patterns of the one or more brain areas.

In some embodiments, particular areas of the brain may respond differently to electrical stimulation. Some areas of the brain may react when stimulation with the depolarization of more neurons than other areas of the brain. The different variance levels of different evoked responses can reflect how different tissues are activated by the settings of the stimulus. The different evoked response variances can then indicate the greater or lesser amounts of neurological tissue reacting to the evoked response, which can be compared to known benchmarks for certain brain areas (e.g., previously established activation patterns). As such, the variance of an evoked response may be used as a parameter for guiding navigation of an electrode in the brain and/or in identifying brain areas.

Variance, as used herein, refers to a measure of how values deviate from an expected value or mean. Below is a formula for calculating variance (where N is the number of values of parameter x, $\mu$ is the mean over N values, and $\sigma^2$ is the variance):

$$\sigma^2 = \frac{\sum (x-\mu)^2}{N}$$

A variance calculation may be performed in several ways. In one way, multiple signals can be sensed at one point in time, such as by multiple electrode combinations along a lead. In this case, multiple electrodes can be used to measure the multiple LFP signals. Multiple electrodes might be grouped together, wherein the volume of neurons measured is based on the closeness of the electrodes (i.e. the further apart the electrodes, the more neurons of brain matter could potentially contribute to the LFP signal). A common parameter of the signals can be measured for the one point in time. For example, the amplitudes of multiple LFP signals can be measured at the same point in time using the multiple LFP signals from different electrodes or electrode combinations. Each variance calculation can be calculated from the multiple amplitude measurements for a common point in time, and the variance calculation can then be repeated for different points in time to determine the difference in variance between the different points in time. Conclusions about the relative levels of neural activation can be made from the differences in variance over time as discussed herein. Therapy configurations, patient states, lead position, and other variables can be changed between the different points in time to measure the differences in activation levels between the different times for which measurements are taken.

Variance may also be calculated using a moving period of time. For example, a window can be defined as having some duration (e.g., five minutes). The window can be moved over a sensed signal, or a sensed signal can be moved through the window, in either case the window framing different intervals of time for calculating different variance values for the different intervals as the window moves. Variance can be calculated periodically for all of the values within the window, and the variance value output can be keyed to the leading edge, trailing edge, or midpoint of the window (e.g., corresponding to the most recent data to enter the window or oldest data in the window) or other feature. The window can move over time (e.g., the window moves consistently with time at the real-time rate that signal data is collected) and a variance value calculated again using all of the parameter values within the window. For example, a calculation can be performed each time data enters/leaves the window or periodically, such as every second, minute, or hour. The intervals of time may be overlapping such that they share some parameter values or may not overlap and therefore not share parameter values. The calculated variance values can then represent variance over time. Conclusions about the relative levels of neural activation for the different intervals can be made based on the differences in variance over the time intervals as discussed herein. Therapy configurations, patient states, lead position, and other variables can be changed between the different intervals to measure the differences in activation between the different intervals for which measurements are taken.

The elements of monitoring, assessing activation, and administering therapy as described herein can be applicable to many brain injury and disease states. Monitored and/or treated areas may concern the brain and may additionally/alternatively concern other neural networks of the body. Tracking of a neurological condition and therapeutic applications include, without limitation, chronic pain, Alzheimer's disease, depression, epilepsy, Parkinson's disease, psychiatric disorders (e.g., schizophrenia), addiction, dystonia, tremor, akinesia, neuralgia, sleep dysfunction, depression, obsessive compulsive disorder, obesity, gastroparesis, urinary or fecal dysfunction, sexual dysfunction, or other neurological disorders.

In some implementations, monitoring of variance is performed before therapy is delivered so that a baseline measure of intrinsic brain variance can be calculated. Later calculations of variance, such as variance during therapy, can be compared to the baseline to determine whether the therapy is causing greater neuron activation or suppressing activation, depending on the therapeutic goal. Brain activation levels can be tracked over long periods of time, such as weeks, months, and years, to assess brain activation levels. For example, the variance of a bioelectrical signal may be periodically calculated for a patient to track the progression of a disease or condition. The disease or condition may be tracked to be worsening if less neuron activation is observed over time (e.g., by determining that variance is decreasing over time) and the disease or condition may be tracked to be improving if greater neuron activation is observed over time (e.g., by determining that variance is increasing over time.) An output can be provided indicating the increase or decrease in activation. The output may be in the form of a number of a normalized scale, wherein all variance values over some time are scaled (e.g., out of a ten point scale) such that the output indicates a number of the normalized scale, which might be easier to understand than a variance value.

Brain areas targeted for assessing neuron activation can be selected based on the pathology of the disease or brain damage of the patient. The targets may be, for example, a damaged or diseased brain area, a brain area known to support a damaged or diseased brain area, and/or a brain area known to substitute a function of a damaged or diseased brain area. In some cases, fMRI can be used to identity these areas. fMRI can further be used to determine which of one or more brain areas are showing insufficient activation, for which the presently disclosed techniques can be targeted. fMRI can map brain activity to a 2D or 3D plot (e.g., on a computer display) allowing activated brain areas to be identified, usually indicated by being colored or otherwise highlighted. While fMRI is used as an exemplar in this disclosure, all other types of neural imaging are contemplated to be used in the same way, including PET and MEG scanning.

Figure 7:
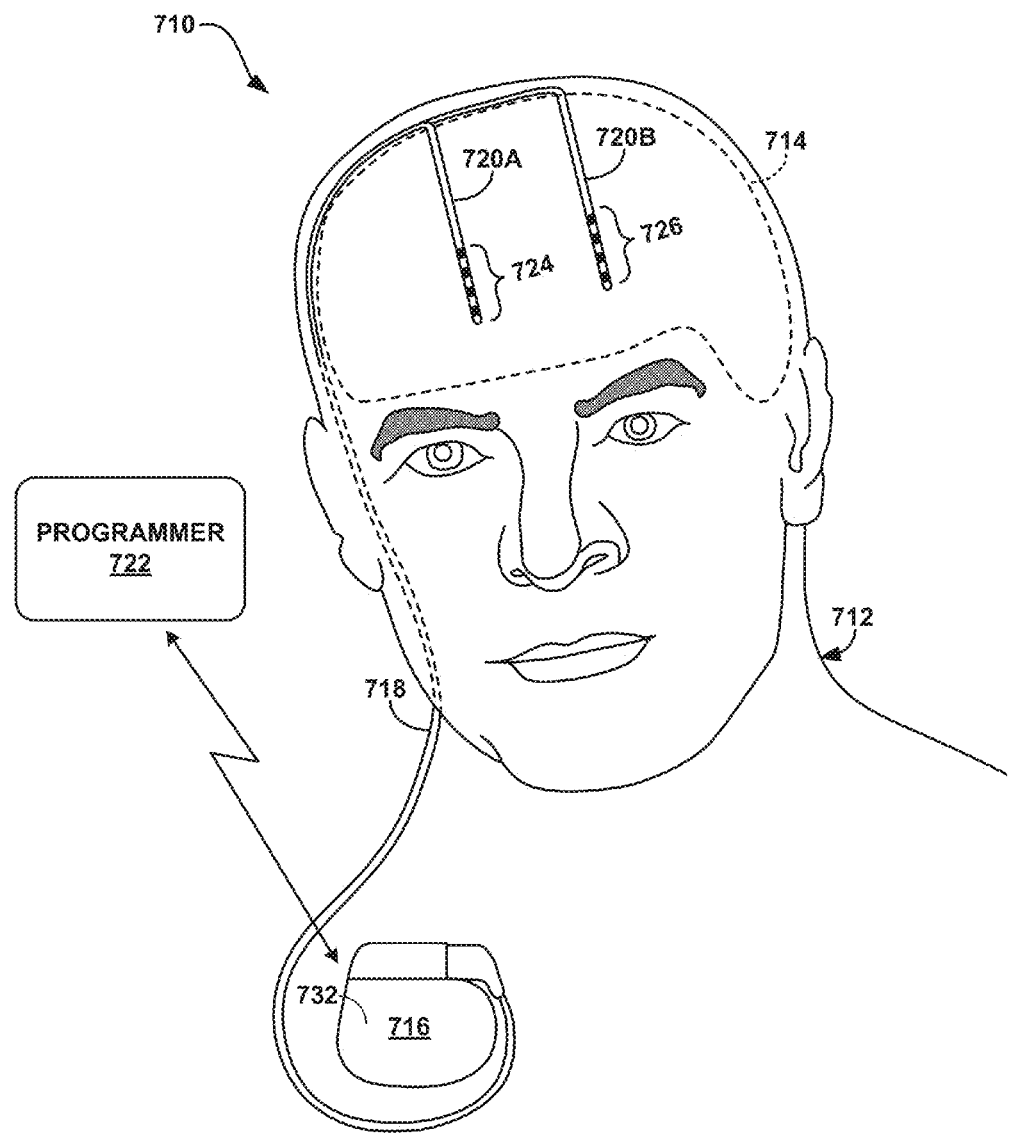
FIG. 7 is a conceptual diagram illustrating an example system.

FIG. 7 is a conceptual diagram illustrating an example therapy system 710 that monitors a brain condition and/or delivers therapy to patient 712 to manage the brain condition. System 710 includes implantable medical device (IMD) 716, lead extension 718, one or more leads 720A and 7209 (collectively "leads 720") with respective sets of electrodes 724, 726 and medical device programmer 722. IMD 716 may include monitoring circuitry in electrical connection with the electrodes 724, 726 of leads 720A and 7209, respectively.

System 710 may monitor one or more bioelectrical signals of patient 712. For example, IMD 716 may include a sensing module (e.g., sensing module 744 of FIG. 8) that senses bioelectrical signals of one or more regions of brain 714. In the embodiment shown in FIG. 7, the signals may be sensed by electrodes 724, 726 and conducted to the sensing module within IMD 716 via conductors within the respective leads 720A, 720B. As described in further detail below, in some embodiments, control circuitry of IMD 716 or another device (e.g., programmer 722) monitors the bioelectrical signals within brain 714 of patient 712 to assess neural activation based on the variance of the amplitude of bioelectrical signal(s) and/or perform the other functions referenced herein including those of FIGS. 1-6. Control circuitry of IMD 716 or another device (e.g., programmer 722) may control delivery of electrical stimulation or other therapy to brain 714 based on bioelectrical signal variance in a manner that treats a brain condition of patient 712.

In some examples, the sensing module of IMD 716 may receive the bioelectrical signals from electrodes 724, 726 or other electrodes positioned to monitor bioelectrical signals of patient 712 (e.g., if housing 732 of IMD 716 is implanted in or proximate brain 714, an electrode of housing 732 can be used to sense bioelectrical signals and/or deliver stimulation to brain 714). Electrodes 724, 726 may also be used to deliver electrical stimulation from stimulation generator 742 to target sites within brain 714 as well as to sense bioelectrical signals within brain 714. However, IMD 716 can also use separate sensing electrodes to sense the bioelectrical signals. In some embodiments, the sensing module of IMD 716 may sense bioelectrical signals via one or more of the electrodes 724, 726 that are also used to deliver electrical stimulation to brain 714. In other embodiments, one or more of electrodes 724, 726 may be used to sense bioelectrical signals while one or more different electrodes 724, 726 may be used to deliver electrical stimulation.

The bioelectrical signals monitored by IMD 716 (and for which variance is calculated) may reflect changes in electrical current produced by the sum of electrical potential differences across brain tissue. Examples of the monitored bioelectrical signals include, but are not limited to, an EEG signal, an ECoG signal, an MEG signal, and/or a LFP signal sensed from within or about one or more regions of brain 714. These and other signals can be used to perform the various functions referenced herein, including determining the volume of synaptic activation by calculating the bioelectrical brain signal variance.

As described in further detail below, IMD 716 may deliver therapy to any suitable portion of brain 714 that may play a role in affecting the activation of neurons in various embodiments. In some embodiments, system 710 may deliver therapy to patient 712 to manage a neurological disorder of patient 712. For example, system 710 may provide therapy to correct a brain disorder and/or manage symptoms of a neurodegenerative brain condition. Patient 712 ordinarily will be a human patient. In some cases, however, system 710 may be applied to other mammalian or non-mammalian non-human patients.

IMD 716 may include a module that includes a stimulation generator 742 that generates and delivers electrical stimulation therapy to one or more regions of brain 714 of patient 712 via the electrodes 724, 726 of leads 720A and 720B, respectively. In the example shown in FIG. 7, system 710 may be referred to as deep brain stimulation system because IMD 716 may provide electrical stimulation therapy directly to tissue within brain 714, e.g., a tissue site under the dura mater of brain 714. In other embodiments, leads 720 may be positioned to sense brain activity and/or deliver therapy to a surface of brain 714, such as the cortical surface of brain 714, or other location in or along the patient 712.

In the example shown in FIG. 7, IMD 716 may be implanted within a subcutaneous pocket below the clavicle of patient 712. In other embodiments, MD 716 may be implanted within other regions of patient 712, such as a subcutaneous pocket in the abdomen or buttocks of patient 712 or proximate the cranium of patient 712. Implanted lead extension 718 is coupled to IMD 716 via a connector block (also referred to as a header), which may include, for example, electrical contacts that electrically couple to respective electrical contacts on lead extension 718. The electrical contacts electrically couple the electrodes 724, 726 carried by leads 720 to IMD 716. Lead extension 718 traverses from the implant site of IMD 716 within a chest cavity of patient 712, along the neck of patient 712 and through the cranium of patient 712 to access brain 714. Generally, IMD 716 is constructed of a biocompatible material that resists corrosion and degradation from bodily fluids. IMD 716 may comprise a hermetic housing 732 to substantially enclose control circuitry components, such as a processor, sensing module, therapy module, and memory. In some implementations, IMD 716 and other components (e.g., leads 720) may be implanted only in the head of the patient (e.g., under the scalp) and not in the chest and neck regions.

Electrical stimulation may be delivered to one or more regions of brain 714, which may be selected based on many factors, such as the type of patient condition for which system 710 is implemented to manage and the relative level of neural activation identified by variance calculations. In some cases, leads 720 may be implanted within the right and left hemispheres of brain 714 (e.g., as illustrated in FIG. 7) while, in other examples, one or both of leads 720 may be implanted within one of the right or left hemispheres. Other implant sites for leads 720 and MD 716 are contemplated. For example, in some examples, IMD 716 may be implanted on or within cranium. In addition, in some examples, leads 720 may be coupled to a single lead that is implanted within one hemisphere of brain 714 or implanted through both right and left hemispheres of brain 714.

Leads 720 may be positioned to deliver electrical stimulation to one or more target tissue sites within brain 714 to manage patient symptoms associated with a disorder of patient 712. Targeted tissues may be the tissues identified as having abnormal neural activation, such as by identification of which area(s) of the brain 714 are associated unusually low or high signal variance. Leads 720 may be implanted to position electrodes 724, 726 at desired locations of brain 714 through respective holes in cranium. Leads 720 may be placed at any location within or along brain 714 such that electrodes 724, 726 are capable of providing electrical stimulation to target tissue sites of brain 714 during treatment. In some embodiments, leads may be placed such that electrodes 724, 726 directly contact or are otherwise proximate targeted tissue of a particular brain area.

In the example shown in FIG. 7, electrodes 724, 726 of leads 720 are shown as ring electrodes. Ring electrodes are typically capable of sensing and/or delivering an electrical field to any tissue adjacent to leads 720 (e.g., in all directions away from an outer perimeter of leads 720). In other examples, electrodes 724, 726 of leads 720 may have different configurations. For example, electrodes 724, 726 of leads 720 may have a complex electrode array geometry that is capable of producing shaped electrical fields. The complex electrode array geometry may include multiple electrodes (e.g., partial ring or segmented electrodes) around the perimeter of each lead 720, rather than a ring electrode. In this manner, electrical brain sensing and/or electrical stimulation may be associated with a specific direction from leads 720 (e.g., in less than the entire outer perimeter of leads 720) to enhance direction sensing and/or therapy efficacy and reduce possible adverse side effects from stimulating a large volume of tissue in the case of stimulation. As such, electrodes can be positioned to preferentially sense from one side of a lead and to stimulate targeted tissue and avoid stimulating non-targeted tissue.

In some embodiments, outer housing 732 of IMD 716 may include one or more stimulation and/or sensing electrodes. For example, housing 732 can comprise an electrically conductive material that is exposed to tissue of patient 712 when IMD 716 is implanted in patient 712, or an electrode can be attached to housing 732. In alternative examples, leads 720 may have shapes other than elongated cylinders as shown in FIG. 7. For example, leads 720 may be paddle leads, spherical leads, bendable leads, or any other type of shape effective in treating patient 712.

In some examples, the location of the electrodes 724, 726 within brain 714 can be determined based on analysis of a bioelectrical signal of the patient sensed via one or more of the electrodes 724, 726. For example, a particular physiological structure (e.g., the amygdala) may exhibit a unique electrical signal (e.g., a particular variance level) and, thus, facilitate positioning of the electrodes of the lead at the desired implant location through monitoring of the bioelectrical signal.

Stimulation generator 742, under the control of processor 740, generates stimulation signals for delivery to patient 712 via selected combinations of electrodes 724, 726. Processor 740 controls stimulation generator 742 according to stimulation programs 752 stored in memory 741 to apply particular stimulation parameter values specified by one or more programs, such as amplitude, pulse width, timing, and pulse rate. In some embodiments, stimulation generator 742 generates and delivers stimulation signals to one or more target portions of brain 714 via a select combination of electrodes 724, 726.

Leads 720 may be implanted within a desired location of brain 714 via any suitable technique, such as through respective burr holes in a skull of patient 712 or through a common burr hole in the cranium. Leads 720 may be placed at any location within brain 714 such that electrodes 724, 726 of leads 720 are capable of sensing electrical activity of the brain areas (e.g., those associated with abnormal or problematic levels of neural activation) and/or providing electrical stimulation to targeted tissue for treatment (e.g., to stimulate to facilitate proper or beneficial levels of neural activation). A lead, as the term is used herein, can be in the form of a probe having one electrode or multiple electrodes, and is not necessarily associated with an implantable device.

In some embodiments, a processor of system 710 (e.g., a processor of programmer 722 or IMD 716) as control circuitry controls delivery of electrical stimulation by activating electrical stimulation, deactivating electrical stimulation, increasing the intensity of electrical stimulation, or decreasing the intensity of electrical stimulation delivered to brain 714 to titrate electrical stimulation therapy to facilitate altering neural activation levels, among any other function referenced herein. Therapy can be started, stopped, and/or changed by a control circuitry in any manner and based on any parameter or finding as discussed herein.

System 710 may also store a plurality of stimulation programs (e.g., a set of electrical stimulation parameter values), and at least one stimulation program may be associated with at least one of increasing and decreasing neural activation. A processor of IMD 716 or programmer 722 may select a stored stimulation program that defines electrical stimulation parameter values for delivery of electrical stimulation to brain 714 based on a characterization of neural activation. Where IMD 716 delivers electrical stimulation in the form of electrical pulses, for example, the stimulation therapy may be characterized by selected pulse parameters, such as pulse amplitude, pulse rate (frequency), and pulse width. In addition, if different electrodes are available for delivery of stimulation, the therapy may be further characterized by different electrode combinations, which can include selected electrodes and their respective polarities.

External programmer 722 wirelessly communicates with 716 as needed to provide or retrieve information. For example, external programmer 722 may receive sensed data and/or information from IMD 716, as well as send therapy program information to IMD 716. Programmer 722 is an external computing device that the user, e.g., the clinician and/or patient 712, may use to communicate with IMD 716. For example, programmer 722 may be a clinician programmer that the clinician uses to communicate with IMD 716 and program one or more therapy programs for IMD 716. Additionally or alternatively, programmer 722 may be a patient programmer that allows patient 712 to input information (e.g., a self evaluated assessment regarding symptoms), select programs, and/or view and modify therapy parameters.

Programmer 722 is a medical device that may be a handheld computing device with a display viewable by the user and an interface for providing input to programmer 722 (i.e., a user input mechanism) and/or displaying information received from the IMD 716. For example, programmer 722 may include a small display screen (e.g., a liquid crystal display (LCD) or a light emitting diode (LED) display) that presents information to the user. In addition, programmer 722 may include a touch screen display, keypad, buttons, a peripheral pointing device or another input mechanism that allows the user to navigate though the user interface of programmer 722 and provide input. A screen (not shown) of programmer 722 may be a touch screen that allows the user to provide input directly to the user interface shown on the display. The user may use a stylus or finger to provide input to the display.

A screen of the programmer 722 may display outputs as described herein, such as an indication that brain activation is increasing, decreasing, or staying the same for a brain area.

In various embodiments, programmer 722 as a medical device may be a larger workstation or a separate application within another multi-function device, rather than a dedicated computing device. For example, the multi-function device may be a notebook computer, tablet computer, workstation, cellular phone, personal digital assistant or another computing device. The circuitry components of programmer 722 and/or other external device(s), such as equivalent circuitry to that of FIG. 8, can be control circuitry as means for performing functions as described herein (e.g., receiving signals from IMD 716 via telemetry, measuring amplitude of the signals, calculating variance, and assessing neural activation levels) including those functions described in association with FIGS. 1-6. Any of the functions described herein may be performed by control circuitry of the IMD 716, control circuitry of programmer 722, or by control circuitry that is distributed between IMD 716 and programmer 722. For example, the control circuitry of IMD 716 may perform the sensing and amplitude measuring functions and then send the amplitude information to control circuitry of the programmer 722 where variance calculations and other functions described herein are performed. The control circuitry of the programmer 722 may then determine therapy adjustments based on the variance information and transmit the therapy adjustments to the control circuitry of the IMD 716, where the control circuitry of the IMD 716 then delivers therapy using the adjustments.

When programmer 722 is configured for use by the clinician, programmer 722 may be used to transmit initial programming information to IMD 716. This initial information may include hardware information, such as the type of leads 720, the arrangement of electrodes 724, 726 on leads 720, the position of leads 720 within brain 714, initial programs defining therapy parameter values, ranges and/or thresholds for closed loop therapy adjustment, and any other information that may be useful for programming into IMD 716. Programmer 722 may also be capable of controlling circuitry of the IMD 716 in carrying out the function described herein, particularly those relating to sensing signals, calculating variance, assessing neural activation, and/or delivering therapy.

The clinician may also store therapy programs within IMD 716 with the aid of programmer 722. During a programming session, the clinician may determine one or more stimulation programs that may effectively bring about a therapeutic outcome that treats a brain condition, such as increasing or decreasing neural activation. For example, the clinician may select one or more electrode combinations with which stimulation is delivered to brain 714 to increase or decrease neural activation. During the programming session, the clinician may evaluate the efficacy of the one or more electrode combinations based on one or more findings of fMRI, patient self-reporting, or LEP, EEG or other signal. In some examples, programmer 722 may assist the clinician in the creation/identification of stimulation programs by providing a methodical system for identifying potentially effective stimulation parameter values, such as by having a predetermined index of levels of neural activation and stimulation parameters predetermined to be particularly effective in increasing or decreasing neural activation according to observed bioelectrical variance patterns. In some examples, the processor of programmer 722 may calculate and display one or more therapy metrics for evaluating and comparing therapy programs available for delivery of therapy from IMD 716 to patient.

Programmer 722 may also provide an indication to patient 712 when therapy is being delivered which may aid the assessment of therapy efficacy. For example, following the delivery of electrical stimulation or sensing of one or more episodes of neural activation being out of a target range, the patient may evaluate whether he or she seems to have symptoms by answering questions presented on the programmer 722. The information may be used to assess whether the neural activation levels are manifesting as something observable by the patient.

Whether programmer 722 is configured for clinician or patient use, programmer 722 is configured to communicate with IMD 716 and, optionally, another computing device, via wireless communication. Programmer 722, for example, may communicate via wireless communication with IMD 716 using radio frequency (RF) telemetry techniques known in the art. Programmer 722 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 722 may also communicate with other programming or computing devices via exchange of removable media, such as magnetic or optical disks, memory cards or memory sticks. Further, programmer 722 may communicate with IMD 716 and another programmer via remote telemetry techniques known in the art, communicating via a local area network (LAN), wide area network (WAN), public switched telephone network (PSTN), or cellular telephone network, for example.

Figure 8:
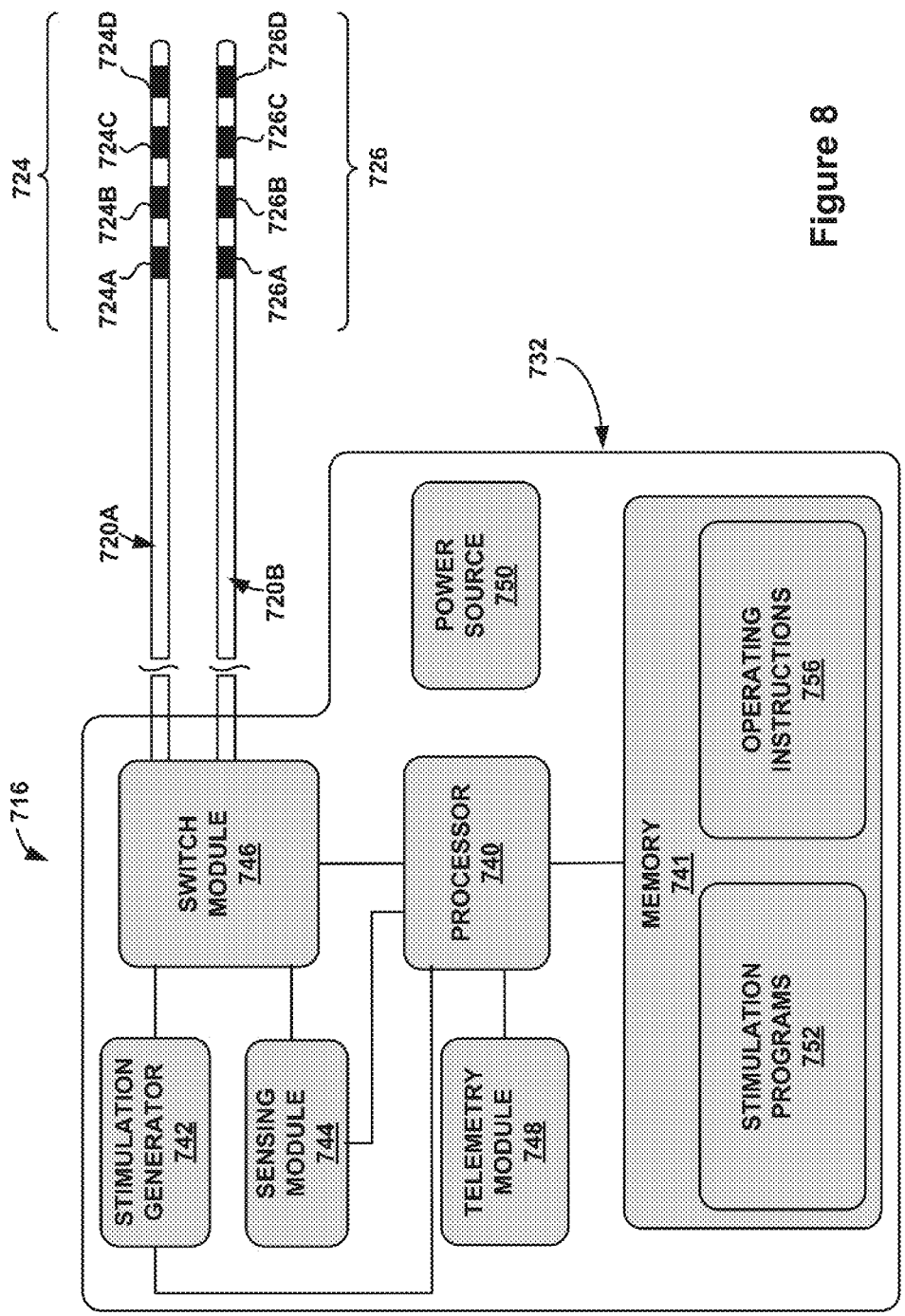
FIG. 8 is a functional block diagram illustrating electrical components of a medical device.

FIG. 8 is a functional block diagram illustrating components of IMD 716. In the configuration shown in FIG. 8, IMD 716 includes processor 740, memory 741, and sensing module 744, which can be control circuitry as means for performing functions as described herein (e.g., sensing signals, measuring amplitude of the signals, calculating variance, and assessing neural activation). Control circuitry may include other circuitry components for carrying out various functions depending on what features the embodiment includes, such as stimulation generator 742 for delivering stimulation. Memory 741 may include any volatile or non-volatile media, such as a random access memory (RAM), read only memory (ROM), non-volatile RAM (NVRAM), electrically erasable programmable ROM (EEPROM), flash memory, and the like. Memory 741 may store computer-readable instructions that, when executed by processor 740, cause IMD 716 to perform various functions described herein. Memory 741 may include operating instructions 756 executable by the processor 740 for causing the IMD 716 to carry out the various functions referenced herein, including those discussed in association with FIGS. 1-6. Memory 741 may store therapy instructions as part of stimulation programs 752 that are available to be selected by processor 740 in response to an indication of a change in brain signal variance from the sensing module 744. In addition, processor 740 may be configured to record diagnostic information, such as sensed signals, measured values, calculated variances, information relating to activation level assessments, brain state episode information, and the like in memory 741 or another memory or storage device. The various functions and options described herein may be performable automatically by the IMD 716 by processor 740 execution of operating instructions 756 and stimulation programs 752 stored in memory 741.

The steps, procedures, techniques, etc. referenced herein may be carried out in part by, for example, software instructions, such as those used to define a software or computer program. The computer-readable medium (e.g., memory 741) may store instructions (e.g., operating instructions 756 and stimulation programs 752) executable by a processor (e.g., processor 740 and/or of an external device) to carry out the steps, procedures, techniques, etc. In this way, control circuitry can be configured to perform the various steps, procedures, techniques, etc. as described herein, including those discussed in association with FIGS. 1-6. The computer-readable medium may be a computer-readable storage medium such as a storage device (e.g., a disk drive, or an optical drive), memory (e.g., a Flash memory, random access memory or RAM) or any other type of volatile or non-volatile memory that stores processor executable instructions (e.g., in the form of a computer program or other executable) as part of control circuitry to carryout the functions described herein.

Processor 740 may calculate the variance of a parameter of a sensed bioelectrical signal, and may further determine if the variance is greater, equal to, or less than one or more a previously determined variance value, a range, a baseline, and/or a threshold, such as a threshold or range associated with insufficient or overactive neural activation levels.

Processor 740 may by configured to cause stimulation generator 742 to deliver electrical stimulation with pulse voltage or current amplitudes, pulse widths, and frequencies (i.e., pulse rates) as part of control circuitry, and electrode combinations specified by the stimulation programs 752 with predetermined delays, e.g., as stored in memory 741. Processor 740 may control stimulation generator 742 to deliver each pulse, or a burst of pulses, according to a different program of the stimulation programs, such that multiple programs of stimulation are delivered on an interleaved or alternating basis, e.g., having different delays or responding to different brain states, based on the assess relative level of neural activation of a brain area based on calculated variance. In some embodiments, processor 740 may control stimulation generator 742 to deliver a substantially continuous stimulation waveform rather than pulsed stimulation.

As shown, the set of electrodes 724 of lead 720A includes electrodes 724A, 72413, 724C, and 7241), and the set of electrodes 726 of lead 720B includes electrodes 726A, 72613, 726C, and 726D. Processor 740 may control switch module 746 to route sensed signals to sensing module 744 and/or apply the stimulation signals generated by stimulation generator 742 to selected combinations of electrodes 724, 726. In particular, switch module 746 may couple stimulation signals to selected conductors within leads 720, which, in turn, deliver the stimulation signals across selected electrodes 724, 726. Switch module 746 may be a switch array, switch matrix, multiplexer, or any other type of switching module configured to selectively couple stimulation energy to selected electrodes 724, 726 and to selectively sense bioelectrical signals with selected electrodes 724, 726. Hence, stimulation generator 742 is coupled to electrodes 724, 726 via switch module 746 and conductors within leads 720. In some embodiments, however, IMD 716 does not include switch module 746.

Sensing module 744 is configured to sense bioelectrical signals of patient 712 via a selected subset of electrodes 724, 726, or with one or more electrodes 724, 726 and at least a portion of a conductive outer housing 732 of IMD 716, an electrode on an outer housing of IMD 716, or another reference. In some embodiments, sensing module 744 may measure the amplitude of a signal and relate the value to processor 740. Processor 740 may control switch module 746 to electrically connect sensing module 744 to selected electrodes 724, 726. In this way, sensing module 744 may selectively sense bioelectrical signals with different combinations of electrodes 724, 726 (and/or a reference other than an electrode 724, 726). Although bioelectrical brain signals are used as an exemplar herein, or sensed signals are also contemplated. Although the electrodes 724, 726 are principally described as being implanted within a brain in the manner of DBS, other locations are additionally or alternatively contemplated. For example, electrodes may be deployed at selected tissue sites or on selected surfaces of a human patient, such as on the brain, along the cortex, proximate the spinal cord, on the scalp, or elsewhere. As an example, scalp electrodes may be used to measure or record EEG signals. As another example, electrodes implanted at the surface of the cortex may be used to measure or record ECoG signals. In some embodiments, an external device may be worn with sensing elements positioned at a desired location adjacent the patient to detect a bioelectrical signal.

Sensing module 744 may form part of a sensor circuit configured to monitor a variety of signals via a variety of different sensing elements, such as a bioelectrical signal via electrodes 724, 726, and/or other physiological signals. Sensing module 744 may include amplifiers, filters, modulators, and other circuitry for conditioning and measuring one or more parameters of signals, such as the amplitude of an LIT signal. Sensing module 744 and/or processor 740 (and/or other circuitry) may monitor the signals to measure the signal amplitude for variance calculation according to any technique referenced herein. In some embodiments, sensing module 744 may directly process signals obtained from electrodes 724, 726 or other sensing elements with little or no preprocessing by other components. In other embodiments, sensing module 744 may include preprocessing circuitry to process or convert signals for analysis by processor 740 or other circuitry. In some embodiments, sensing module 744 includes circuitry configured to measure one or more parameters of an electrical signal, such as amplitude, and processor 740 receives an output from the telemetry module 748 of an indication of the measurement for further analysis as discussed herein, such as variance calculation and further determination of whether the variance exceeds a threshold or is within a target range.

While the embodiment of FIG. 8 illustrates stimulation generator 742 and stimulation programs 752, various embodiments do not include stimulation circuitry. For example, various embodiments are directed to sensing brain signals and assessing a relative level of neural activation of a brain area based on variance to track a brain condition or disease, but not treating that condition or disease by electrical stimulation from the same device. In some embodiments, stimulation generator 742 and stimulation programs 752 can be replaced by drug delivery components and drug delivery programs, such as by using drug pump technology. As such, IMD 716 and the circuitry described in association with IMD 716 (e.g., that of FIG. 8) are adaptable for controlling drug delivery based on variance over time of a bioelectrical brain signal.

Processor 740 as part of control circuitry may monitor bioelectrical signals sensed by sensing module 744 in any suitable manner in order to assess the relative level of neural activation of a brain area based on variance. For example, sensing module 744 may directly sense one or more bioelectrical signals, e.g., a LFP, via one or more of electrodes 724, 726 at a particular point within a portion of brain 714, and processor 740 may monitor the bioelectrical signal. Memory 741 may store information related to threshold values for signal characteristics that demarcate abnormally low or high activation levels by variance thresholds, and processor 740 may compare calculated variance values with stored threshold values to track a disease or condition and/or administer therapy.

In various embodiments, system 710 may include one or more external electrodes positioned on the outer surface of the cranium of patient 712 that can sense bioelectrical activity and generate a bioelectrical signal that can be used to assess the relative level of neural activation of a brain area based on variance. Such assessment may use the techniques discussed herein for assessing the relative level of neural activation of a brain area based on variance via internally sensed signals.

Although sensing module 744 is incorporated into a common housing 732 with stimulation generator 742 and processor 740, in other examples, sensing module 744 is in a physically separate outer housing from outer housing 732 of IMD 716 and communicates with processor 740 via wired or wireless communication techniques.

Sensing of brain signals and detecting events, among other things, can be implemented in view of commonly assigned U.S. Provisional Patent Application No. 61/527,387, filed on Aug. 25, 2011, by Carlson et al., titled METHOD AND APPARATUS FOR DETECTING A BIOMARKER IN THE PRESENCE OF ELECTRICAL STIMULATION, which is incorporated by reference herein in its entirety. Furthermore, setting algorithms for event detection, among other things, can be implemented in view of commonly assigned U.S. Pat. App. No. 2010/0280335 to Carlson et al., which is entitled "PATIENT STATE DETECTION BASED ON SUPERVISED MACHINE LEARNING BASED ALGORITHM" filed Nov. 4, 2010; and U.S. Pat. App. No. 2010/0280334 to Carlson et al., which is entitled "PATIENT STATE DETECTION BASED ON SUPPORT VECTOR MACHINE BASED ALGORITHM" filed Nov. 4, 2010, which are incorporated herein by reference in their entireties.

Telemetry module 748 supports wireless communication between IMD 716 and an external programmer 722 or another computing device under the control of processor 740. Processor 740 of IMD 716 may receive, as updates to sensing and/or stimulation programs, variance thresholds and values for stimulation parameters such as amplitude and electrode combination information from programmer 722 via telemetry module 748. The updates to the stimulation, sensing, or other programs may be stored within stimulation programs 752 or other section of memory 741. Telemetry module 748 in IMD 716, as well as telemetry modules in other devices and systems described herein, such as programmer 722, may accomplish communication by RF communication or inductance techniques, among other transcutaneous communication techniques. For example, telemetry module 748 may communicate with external medical device programmer 722 via proximal inductive interaction of IMD 716 with programmer 722. Accordingly, telemetry module 748 may send information to external programmer 722 on a continuous basis, at periodic intervals, or upon request from IMD 716 or programmer 722. For example, processor 740 may transmit sensed signals and/or network activation information to programmer 722 via telemetry module 748.

Power source 750 delivers operating power to various components of IMD 716. Power source 750 may include a small rechargeable or non-rechargeable battery and a power generation circuit to produce the operating power. Recharging may be accomplished through proximal inductive interaction between an external charger and an inductive charging coil within IMD 716. In some examples, power requirements may be small enough to allow IMD 716 to utilize patient motion and implement a kinetic energy-scavenging device to trickle charge a rechargeable battery. In various embodiments, traditional batteries may be used.

The techniques described in this disclosure, including those attributed to programmer 722, IMD 716, processor, control circuitry or various constituent components, may be implemented, at least in part, in hardware, software, firmware or any combination thereof. Such hardware, software, firmware may be implemented within the same device or within separate devices to support the various operations and functions described in this disclosure. While the techniques described herein are primarily described as being performed by processor 740 of IMD 716 and/or processor of a programmer or other external device as part of control circuitry, any of the one or more parts of the techniques described herein may be implemented by a processor of one of IMD 716, programmer 722, or another computing device, alone or in combination with each other, as control circuitry. For example, the various functional options discussed in connection with FIGS. 1-6 and elsewhere herein can be implemented by a processor (e.g., processor 740) executing program instruction stored in memory (e.g., memory 741), as control circuitry, that performs the various described functions.

Although the control circuitry of FIG. 8 is generally illustrated and described in terms of an implantable medical device, the control circuitry could alternatively be embodied in an at least partially external device and, depending on the therapy and/or circuitry configuration, may be wholly external.

The techniques described in this disclosure, including those of FIGS. 1-8 and those attributed to programmer, IMD, processor, and/or control circuitry, or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., a processor and memory having stored program instructions executable by the processor as control circuitry configured to carryout one or more specified functions). The functions referenced herein and those functions of FIGS. 1-8, may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an IMD and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

While Parkinson's disease is used as an exemplar for describing various aspects of the present disclosure, it is contemplated that the techniques and devices could be applied to other brain conditions, such as cognitive impairment and traumatic brain damage, among others. Furthermore, it is contemplated that various brain conditions may be characterized by the abnormally low or high neural activity. Moreover, while brain conditions and diseases are used as examples herein for discussion of the concepts and features of the present disclosure, the technique of using variance of a bioelectrical signal to determine the relative amount of electrically active biological elements is applicable to other cellular structures. For example, the variance of the amplitude of electrical cardiogram signals could be used to determine the relative amount of cardiac muscle cells depolarizing. As such, the options and features discussed herein (e.g., those associated with FIGS. 1-8), including injury and disease tracking as well as therapy titration, are applicable to cardiac and other bioelectrical systems. One having ordinarily skill in the art will appreciate that the various techniques, options, features, and components discussed herein are applicable to various embodiments, such as in implementation by an IMD or external device having appropriately configured control circuitry.

Various examples have been described. These and other examples are within the scope of the following claims.

We claim:

1. A method for assessing neural activation of a brain, comprising:
    sensing one or more bioelectrical signals from one or more electrodes in contact with or proximate the brain;
    measuring the amplitude of the one or more bioelectrical signals over a period of time;
    calculating a plurality of variance values from the amplitude of the one or more bioelectrical signals, each of the variance values of the plurality corresponding to the variance of the amplitude for a different interval of time of the period of time with respect to the other variance values of the plurality of variance values; and
    assessing the relative level of neural activation of an area of the brain based on the plurality of variance values, wherein the area of the brain is assessed to have a higher level of neural activation when the variance is higher as compared to the level of neural activation when the variance is lower and wherein sensing, measuring, calculating, and assessing are each performed at least in part by control circuitry;
    wherein assessing the relative level of neural activation of the area of the brain comprises estimating the functional synaptic volume of the area of the brain.

2. The method of claim 1, wherein assessing the relative level of neural activation of the area of the brain comprises comparing the plurality of variance values and determining whether the variance has increased or decreased within the period of time, wherein the level of neural activation is assessed to have increased within the period of time if the variance increased and the level of neural activation is assessed to have decreased within the period of time if the variance decreased.

3. The method of claim 1, wherein assessing the relative level of neural activation comprises:
   setting one or more of a variance baseline, variance threshold, or a variance range based on at least some of the plurality of variance values; and
   determining whether one or more of the variance values deviate from one or more of the variance baseline, the variance threshold, or the variance range.

4. The method of claim 1, further comprising tracking the effectiveness of a therapy based on the assessment of the relative level of neural activation of the area of the brain.

5. The method of claim 4, wherein therapy is indicated to be at least somewhat effective if the variance of the amplitude of the one or more bioelectrical signals changes relative to a baseline variance associated with a lesser amount of the therapy or no therapy.

6. The method of claim 1, further comprising titrating one or both of an electrical stimulation therapy or a drug therapy based on the assessment of the relative level of neural activation of the area of the brain.

7. The method of claim 1, further comprising tracking a brain condition based on the assessment of the relative level of neural activation of the area of the brain, wherein the brain condition is associated with one or both of an injury and a disease.

8. The method of claim 1, further comprising determining the location of the one or more electrodes in the brain based on the assessment of the relative level of neural activation of the area of the brain.

9. The method of claim 1, wherein the one or more bioelectrical signals comprise local field potential signals.

10. A system comprising:
    a lead;
    one or more electrodes that are on the lead and are configured to sense bioelectrical activity of a brain; and
    control circuitry configured to:
       sense one or more bioelectrical signals using the one or more electrodes;
       measure the amplitude of the one or more bioelectrical signals over a period of time;
       calculate a plurality of variance values from the amplitude of the one or more bioelectrical signals, each of the variance values of the plurality corresponding to the variance of the amplitude for a different interval of time of the period of time with respect to the other variance values of the plurality of variance values; and
       assess the relative level of neural activation of an area of the brain based on the plurality of variance values, wherein the area of the brain is assessed to have a higher level of neural activation when the variance is higher as compared to the level of neural activation when the variance is lower;
    wherein the control circuitry is further configured to assess the relative level of neural activation of the area of the brain by estimating the functional synaptic volume of the area of the brain.

11. The system of claim 10, wherein the control circuitry is configured to assess the relative level of neural activation of the area of the brain by comparing the plurality of variance values and determining whether the variance has increased or decreased within the period of time, wherein the level of neural activation is assessed to have increased within the period of time if the variance increased and the level of neural activation is assessed to have decreased within the period of time if the variance decreased.

12. The system of claim 10, wherein the control circuitry is configured to assess the relative level of neural activation of the area of the brain by:
    setting one or more of a variance baseline, a variance threshold, or a variance range based on at least some of the plurality of variance values; and
    determining whether one or more of the variance values deviate from one or more of the variance baseline, the variance threshold, or the variance range.

13. The system of claim 10, wherein the control circuitry is further configured to track the effectiveness of a therapy based on the assessment of the relative level of neural activation of the area of the brain.

14. The system of claim 13, wherein the therapy is indicated to be at least somewhat effective if the variance of the amplitude of the one or more signals changes relative to a baseline variance associated with a lesser amount of the therapy or no therapy.

15. The system of claim 10, wherein the control circuitry is further configured to titrate one or both of an electrical stimulation therapy or a drug therapy based on the assessment of the relative level of neural activation of the area of the brain.

16. The system of claim 10, wherein the control circuitry is further configured to track a brain condition based on the assessment of the relative level of neural activation of the area of the brain and provide an output on a display based on the tracking of the brain condition, wherein the brain condition is one or both of an injury and a disease.

17. The system of claim 10, wherein the control circuitry is further configured to determine the location of the one or more electrodes based on the assessment of the relative level of neural activation of the area of the brain and indicate the location on a display.

18. The system of claim 10, wherein the one or more signals comprise local field potential signals.

19. A system for assessing activation of a brain, comprising:
    means for sensing one or more bioelectrical signals from a brain;
    means for measuring the amplitude of the one or more bioelectrical signals over a period of time;
    means for calculating a plurality of variance values from the amplitude of the one or more bioelectrical signals, each of the variance values of the plurality corresponding to the variance of the amplitude for a different interval of time of the period of time with respect to the other variance values of the plurality of variance values; and
    means for assessing the relative level of neural activation of an area of the brain based on the plurality of variance values, wherein the area of the brain is assessed to have a higher level of neural activation when the variance is higher as compared to the level of neural activation when the variance is lower; and
    wherein the means for assessing comprises means for assessing the relative level of neural activation of the area of the brain by estimating the functional synaptic volume of the area of the brain.

* * * * *